US006667065B1

(12) United States Patent
Kragh et al.

(10) Patent No.: US 6,667,065 B1
(45) Date of Patent: Dec. 23, 2003

(54) NON-MALTOGENIC EXOAMYLASES AND THEIR USE IN RETARDING RETROGRADATION OF STARCH

(75) Inventors: Karsten M. Kragh, Viby J. (DK); Bjarne Larsen, Viby J (DK); Preben Rasmussen, Kirke Hyllinge (DK); Lene Duedahl-Olesen, Aalborg (DK); Wolfgang Zimmermann, Chemnitz (DE)

(73) Assignee: Danisco A/S, Copenhagen (DK)

( * ) Notice: Subject to any disclaimer, the term of this patent is extended or adjusted under 35 U.S.C. 154(b) by 0 days.

(21) Appl. No.: 09/647,504

(22) PCT Filed: Mar. 30, 1999

(86) PCT No.: PCT/IB99/00649

§ 371 (c)(1),
(2), (4) Date: Feb. 28, 2001

(87) PCT Pub. No.: WO99/50399

PCT Pub. Date: Oct. 7, 1999

(30) Foreign Application Priority Data

Apr. 1, 1998 (DK) .............................................. 0457/98

(51) Int. Cl.$^7$ ................................................ A21D 8/04

(52) U.S. Cl. ........................................ 426/28; 426/549

(58) Field of Search ........................... 426/20, 549, 28, 426/653

(56) References Cited

U.S. PATENT DOCUMENTS

| 4,946,779 A | 8/1990 | Kameda et al. |
| 5,204,254 A | 4/1993 | Schmid et al. ............... 435/202 |
| 6,242,224 B1 * | 6/2001 | Nakano et al. ................ 435/99 |

FOREIGN PATENT DOCUMENTS

| EP | 0 298 645 | 1/1989 |
| EP | 0 412 607 | 2/1991 |
| EP | 0 494 233 | 7/1992 |
| JP | 6-279745 | 10/1994 |
| JP | 6-279746 | 10/1994 |
| WO | 91/04669 | 4/1991 |

OTHER PUBLICATIONS

Zhou et al. "Properties of the enzyme expressed by the *Pseudomonas saccharophila* maltotetraohydrolase gene (mta) . . . "; Car Research, vol. 223; pp. 255–261, Jan. 1992.*

Byoung–Cheol Min et al., "Cloning of Novel Maltooligosaccharide–Producing Amylases as Antistaling Agents for Bread.", Journal Agriculture Food Chemistry, vol. 46, pp. 779–782, 1998.

Jakubczyk et al., "Studies On The Application Of Some Amylolytic Preparations In The Production Of Wheat Bread", Scientific transactions of the Academy of Agriculture in Warsaw, Agricultural and Food Technology, vol. 8:223–235, (1973).

Fogarty, "Microbial Amylases," *Microbial Enzymes and Biotechnology* (1983), Fogarty, ed., pp. 1–92.

Fogarty et al., "Starch–Degrading Enzymes of Microbial Origin," *Progress in Industrial Microbiology* (1979), Bull, ed., pp. 87–150.

Kainuma et al, "Isolation and Action Pattern of Maltohexaose Producing amylase from *Aerobacter Aerogenes,*" *FEBS Letters* (1971), vol. 26, No. 1, pp. 281–285.

Monma et al., "Formation and Hydrolysis of Maltohexaose by an Extracellular Exo–maltohexaohydrolase," *Agric. Biol. Chem.* (1983), vol. 47, No. 8, pp. 1769–1774.

Kennedy et al., "Characteristics of alpha–Amylase K, a Novel Amylase from a sTrain of *Bacillus subtilis,*" *Starch/Stärke* (1979), vol. 31, No. 3, pp. 93–99.

Takasaki, "Production of Maltohexaose by α–amylase from *Bacillus circulans* G–6," *Agric. Biol. Chem.* (1982), vol. 46, No. 6, pp. 1539–1547.

Taniguchi et al., "Purification of *Bacillus circulans* F–2 Amylase and its General Properties," *Agric. Biol. Chem.* (1983), vol. 47, No. 3, pp. 511–519.

Taniguchi, "Maltohexaose–Producing Amylase of *Bacillus circulans* F–2," *Biotechnology of Amylodextrin Oligosaccharides* (1989), Friedman, ed., pp. 111–124.

Bealin–Kelly et al., "The α–amylase of the caldoactive bacterium *Bacillus caldovelox,*" *Biochemical Society Transactions* (1990), vol. 18, No. 2, pp. 310–311.

Fogarty et al., "A novel maltohexaose–forming α–amylase from *Bacillus caldovelox*: patterns and mechanisms of action," *App. Microbiol. Biotechnol.* (1991), vol. 36, pp. 184–189.

Saito, "A Thermophilic Extracellular α–Amylase from *Bacillus licheniformis,*" *Archives of Biochemistry and Biophysics* (1973), vol. 155, pp. 290–298.

Okemoto et al., "Isolation and cultivation of a novel microorganism producing a maltopentaose–forming enzyme," *Appl. Microbiol. Biotechnol.* (1986), vol. 25, pp. 137–142.

(List continued on next page.)

*Primary Examiner*—Keith Hendricks
(74) *Attorney, Agent, or Firm*—Foley & Lardner

(57) ABSTRACT

The present invention relates to a process for making a bread product. The process includes the addition of a non-maltogenic exoamylase that hydrolyses starch to a starch medium, and the application of heat to the starch medium. The non-maltogenic exomylase cleaves one or more linear malto-oligosaccharides, predominantly consisting of from four to eight D-glucopyranosyl units, from non-reducing ends of amylopectin side chains. The non-maltogenic exoamylase has an endoamylase activity of less than 0.5 endoamylase units (EAU) per unit of exoamylase activity.

15 Claims, 7 Drawing Sheets

OTHER PUBLICATIONS

Shida et al., "Cloning and Nucleotide Sequence of the Maltopentaose–forming Amylase Gene from Pseudomonas sp. KO–8940," *Biosci. Biotech. Biochem.* (1992), vol. 56, No. 1, pp. 76–80.

Sakano et al., "Purification and Properties of an exo–α–Amylase from *Pseudomonas stutzeri*," *Agric. Biol. Chem.* (1982), vol. 46, No. 3, pp. 639–646.

Takasaki et al., "Maltotetraose–producing Amylase from Bacillus sp. MG–4," *Agric. Biol. Chem.* (1991), vol. 55, No. 7, pp. 1715–1720.

Fogarty et al., "Extracellular Maltotetraose–Forming Amylase of Pseudomonas sp. IMD 353," *Biotechnology Letters* (1994), vol. 16, No. 5, pp. 473–478.

Wako et al., "Purification and some Properties of a Maltotriose–producing Amylase," *J. Jap. Soc. Starch Sci.* (1979), vol. 26, No. 3, pp. 175–181.

Takasaki, "An Amylase Producing Maltotriose from *Bacillus subtilis*," *Agric. Biol. Chem.* (1985), vol. 49, No. 4, pp. 1091–1097.

McTigue et al., "The alkaline amylase of the alkolophilic Bacillus sp. IMD 370," *Enzyme and Microbial Technology* (1995), vol. 17, pp. 570–573.

Hayashi et al., "Properties of new alkaline maltohexaose–forming amylases," *Appl. Microbiol. Biotechnol.* (1988), vol. 28, pp. 281–285.

Kim et al., "Purification and Characterization of a Maltotetraose–Forming Alkaline α–Amylase from an alkalophilic Bacillus Strain, GM8901," *Applied and Environmental Microbiology* (1995), vol. 61, No. 8, pp. 3105–3112.

Chandra et al, "Production of Extracellular Thermostable α–Amylase by *Bacillus licheniformis*," *J. Ferment. Technol.* (1980), vol. 58, No. 1, pp. 1–10.

Srivastava et al., "Culture Conditions for Production of Thermostable Amylase by *Baciclus stearothermophilus*," *Applied Environmental Microbiology* (1986), vol. 52, No. 1, pp. 179–184.

Planchot et al, "Purification and characterization of extra cellular alpha–amylase from *Aspergillus fumigatus*," *Carbohydrate Research* (1995), vol. 272, pp. 97–109.

Ohnishi et al., "General considerations for conditions and methods of Amylase Assay," *Handbook of Amylases and Related Enzymes* (1988), The Amylase Research Society of Japan, ed., pp. 10–14.

Larsen et al., "Purfication and characterisation of cyclodextrin glycosyltransferase from Paenibacillus sp. F8," *Carbohydrate Research* (1998), vol. 310, pp. 211–219.

Blum et al., "Improved silver staining of plant proteins, RNA and DNA in polyacrylamide gels," *Electrophoresis* (1987), vol. 8, pp. 93–99.

Fuwa, "A new mthod for microdetermination of amylase activity by the use of amylose as the substrate," *The Journal of Biochemistry* (1954), vol. 41, No. 5, pp. 583–603.

Tsukamoto et al., "Nucleotide Sequence of the Maltohexaose–producing amylase gene from an alkalophicic Bacillus sp. #707 and structural similarity to liquefying type α–amylases," *Biochemical and Biophysical Research Communications* (1988), Voo. 151, No. 1, pp. 25–31.

Kainuma et al., "Purification and some properties of a novel maltohexaose–producing exo–amylase from *aerobacter aerogenes*," *Biochimica et Biophysica Acta* (1975), Vo. 410, pp. 333–346.

Lee, "Carbohydrate analyses with high–performance anion–exchange chromatography," *Journal of Chromatography* (1996), vol. 720, pp. 137–149.

Ammeraal et al., "High–performance anion–exchange chromatography with pulsed amperometric detection of linear and branched glucose oligosaccharides," *Carbohydrate Research* (1991), vol. 215, pp. 179–192.

Zhou et al., "Nucleotide sequence of the maltotetraohydrolase gene from *Pseudomonas saccharophila*," *FEBS Letters* (1989), vol. 255, No. 1, pp. 37–41.

Zhou et al., "Properties of the enzyme expressed by the *Pseudomonas saccharophila* maltotetraohydrolase gene (mta) in *Escherichia coli*," *Carbohydrate Research* (1992), vol. 223, pp. 255–261.

Winter et al., "Man–made antibodies," *Nature* (1991), vol. 349, pp. 293–299.

Orlandi et al., "Cloning immunoglobulin variable domains for expression by the polymerase chain reaction," *Proc. Natl. Acad. Sci. USA* (1989), vol. 86, pp. 3833–3837.

Takeda et al., "Construction of chimaeric processed immunoglobulin genes containing mouse variable and human constant region sequences," *Nature* (1985), vol. 314, No. 4, pp. 452–454.

Neuberger et al., "Recombinant antiboies possessing novel effector functions," *Nature* (1984), vol. 312, pp. 604–608.

Morrison et al., "Chimeric human antibody molecules: Mouse antigen–binding domains with human constant region domains," *Proc. Natl. Acad. Sci.* (1984), vol. 81, pp. 6851–6855.

Cole et al., "The EBV–Hybridoma Technique and its Application to Human Lung Cancer," *Monoclonal Antibodies and Cancer Therapy* (1985), Reisfeld et al. editor, pp. 77–96.

Cote et al., "Generation of human monoclonal antibodies reactive with cellular antigens," *Proc. Natl. Acad. Sci.* (1983), vol. 80, pp. 2026–2030.

Kozbor et al., "The production of monoclonal antibodies from human lymphocytes," *Immunology Today* (1983), vol. 4, No. 3, pp. 72–79.

Köhler et al., "Continuous cultures of fused cells secreting antibody of predefined specificity," *Nature* (1975), vol. 256, pp. 495–497.

* cited by examiner

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Mta pos
      213-233 pcr primer

<400> SEQUENCE: 1
atgacgaggt cctttgtttt c                                            21

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Mta pos
      2403-2386 pcr primer

<400> SEQUENCE: 2
gctcctgata cgacagcg                                                18

<210> SEQ ID NO 3
<211> LENGTH: 27
```

```
<212> TYPE: DNA
<213> ORGANISM: Artificial Sequence
<220> FEATURE:
<223> OTHER INFORMATION: Description of Artificial Sequence: Mta pos
      663-683 pcr primer

<400> SEQUENCE: 3
gccatggatc aggccggcaa gagcccg                                      27

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Mta pos
      2258-2238 pcr primer

<400> SEQUENCE: 4
tggatcctca gaacgagccg ctggt                                        25

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Mta pos
      999-982 pcr primer

<400> SEQUENCE: 5
catcgtagag cacctcca                                                18

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Mta pos
      1382-1400 pcr primer

<400> SEQUENCE: 6
gatcatcaag gactggtcc                                               19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Mta pos
      1439-1421 pcr primer

<400> SEQUENCE: 7
cttgagagcg aagtcgaac                                               19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Mta pos
      1689-1708 pcr primer

<400> SEQUENCE: 8
gacttcatcc gccagctgat                                              20
```

US 6,667,065 B1

NON-MALTOGENIC EXOAMYLASES AND THEIR USE IN RETARDING RETROGRADATION OF STARCH

This application is a 371 National Stage of PCT/IB99/00649, filed Mar. 30, 1999.

FIELD OF THE PRESENT INVENTION

The present invention relates to proteins, especially proteins that are capable of degrading starch.

In particular, the present invention relates to the use of proteins that are capable of retarding the detrimental retrogradation of starch.

Detrimental retrogradation processes, such as staling, typically occur after the heating and cooling of starch media, in particular aqueous starch suspensions, and are due to transformation of gelatinised starch to an increasingly ordered state.

More in particular, the present invention relates to the use of proteins that are capable of retarding the detrimental retrogradation of amylopectin.

More in particular, the present invention relates to the use of proteins to prepare baked bread products, as well as to the baked bread products themselves.

More in particular, the present invention relates to retardation of staling in baked farinaceous bread products.

More specifically the present invention relates to a process for making a baked farinaceous bread product having retarded or reduced staling, comprising adding a non-maltogenic exoamylase to the bread dough.

The present invention also relates to an improver composition for dough and baked farinaceous bread products comprising a non-maltogenic exoamylase.

BACKGROUND OF THE PRESENT INVENTION

Starch comprises amylopectin and amylose. Amylopectin is a highly branched carbohydrate polymer with short α-(1→4)-D-glucan chains which are joined together at branch points through α-(1→6) linkages forming a branched and bushlike structure. On average, there is one branch point for every 20–25 α-(1→4) linked glucose residues. In contrast, amylose is a linear structure mainly consisting of unbranched α-(1→4)-D-glucan units. Typically, starches contain about 75% amylopectin molecules and about 25% amylose molecules.

More specifically, linear malto-oligosaccharides are composed of 2–10 units of α-D-glucopyranose linked by an α-(1→4) bond. Due to their properties such as low sweetness, high waterholding capacity, and prevention of sucrose crystallisation [1] these compounds have potential applications in the food industry. The preparation of malto-oligosaccharides with a degree of polymerisation (DP) above 3 (i.e. DP>3) in larger amounts is however tedious and expensive.

As background information, DP1=glucose, DP2=maltose, DP3=maltotriose, DP4=maltotetraose, DP5=maltopentaose, DP6=maltohexaose, DP7=maltoheptaose, DP8=maltooctaose, DP9=maltononaose, and DP10=maltodecaose.

The discovery of microbial enzymes, which produce malto-oligosaccharides of a specific length could allow the production of larger amounts of these oligosaccharides [2].

Amylases are starch-degrading enzymes, classified as hydrolases, which cleave α-D-(1→4) O-glycosidic linkages in starch. Generally, α-amylases (E.C. 3.2.1.1, α-D-(1→4)-glucan glucanohydrolase) are defined as endo-acting enzymes cleaving α-D-(1→4) O-glycosidic linkages within the starch molecule in a random fashion [3]. In contrast, the exo-acting amylolytic enzymes, such as β-amylases (E.C. 3.2.1.2, α-D-(1→4)-glucan maltohydrolase), and some product-specific amylases cleave the starch molecule from the non-reducing end of the substrate [4]. β-Amylases, α-glucosidases (E.C. 3.2.1.20, α-D-glucoside glucohydrolase), glucoamylase (E.C. 3.2.1.3, α-D-(1→4)-glucan glucohydrolase), and product-specific amylases can produce malto-oligosaccharides of a specific length from starch.

Several amylases producing malto-oligosaccharides of a specific DP have been identified previously including maltohexaose-producing amylases from *Klebsiella pneumonia* [5, 6], *Bacillus subtilis* [7], *B. circulans* G-6 [8], *B. circulans* F-2 [9, 10], and *B. caldovelox* [11, 12]. Maltopentaose-producing amylases have been detected in *B. licheniformis* 584 [13] and *Pseudomonas* spp. [14, 15]. Furthermore, maltotetraose-producing amylases have been reported from *Pseudomonas stutzeri* NRRL B-3389 [16, 17], *Bacillus* sp. MG-4 [18] and *Pseudomonas* sp. IMD353 [19] and maltotriose-producing amylases from *Streptomyces griseus* NA-468 [20] and *B. subtilis* [21].

EP-B1-298,645 describes a process for preparing exo-maltotetraohydrolase of *Pseudomonas stutzen* or *P. saccharophila* using genetic engineering techniques.

U.S. Pat. No. 5,204,254 describes a native and a genetically modified exo-maltopentao-hydrolase of an alkalophilic bacterium (DSM 5853).

Very few product-specific amylases active at high pH have been identified. Examples of those that have been identified include amylases from *Bacillus* sp. H-167 producing maltohexaose [22, 23], from a bacterial isolate (163-26, DSM 5853) producing maltopentaose [24], from *Bacillus* sp. IMD370 producing maltotetraose and smaller malto-oligosaccharides [25], and from *Bacillus* sp. GM 8901 that initially produced maltohexaose from starch which was converted to maltotetraose during extended hydrolysis periods [26].

Starch granules heated in the presence of water undergo an order-disorder phase transition called gelatinization, where liquid is taken up by the swelling granules.

Gelatinization temperatures vary for different starches and depend for the native, unmodified starches on their biological source.

Cooling converts the gelatinised phase into a viscoelastic paste or elastic gel, depending on the starch concentration. During this process, amylose and amylopectin chains reassociate to form a more ordered structure. With time, more associations are formed and they become even more ordered. It is believed that associations of amylopectin chains DP 15–20 lead to a thermoreversible, quasi-crystalline structure.

In consequence of detrimental retrogradation, the water-holding capacity of the paste or gel system is changed with important implications on the gel texture and dietary properties.

It is known that the quality of baked bread products gradually deteriorates during storage. The crumb loses softness and elasticity and becomes firm and crumbly. This so-called staling is primarily due to the detrimental retrogradation of starch, which is understood to be a transition of the starch gelatinised during baking from an amorphous state to a quasi crystalline state. The increase in crumb firmness is often used as a measure of the staling process of bread.

Upon cooling of freshly baked bread the amylose fraction, within hours, retrogrades to develop a network. This process is beneficial in that it creates a desirable crumb structure with a low degree of firmness and improved slicing properties. More gradually crystallisation of amylopectin takes place within the gelatinised starch granules during the days after baking. In this process amylopectin is believed to reinforce the amylose network in which the starch granules are embedded. This reinforcement leads to increased firmness of the bead crumb. This reinforcement is one of the main causes of bread staling.

The rate of detrimental retrogradation or crystallisation of amylopectin depends on the length of the side chains of amylopectin. In accordance with this, cereal amylopectin retrogrades at a slower rate than amylopectin from pea or potato, which has a longer average chain length than cereal amylopectin.

This is supported by observations from amylopectin gel systems that amylopectin with average chain length of DP, i.e. degree of polymerisation, $\leq 11$ do not crystallise at all. Furthermore the presence of very short chains of DP 6–9 seems to inhibit the crystallisation of surrounding longer side chains probably because of steric hindrance. Thereby these short chains seem to have a strong anti-detrimental retrogradation effect. In accordance with this, amylopectin retrogradation is directly proportional to the mole fraction of side chains with DP 14–24 and inversely proportional to the mole fraction of side chains with DP 6–9.

In wheat and other cereals the external side chains in amylopectin are in the range of DP 12–19. Thus, enzymatic hydrolysis of the amylopectin side chains can markedly reduce their crystallisation tendencies.

It is known in the art to retard the staling of bread by using glucogenic and maltogenic exo-amylases—such as amylo-gycosidases which hydrolyse starch by releasing glucose—and maltogenic exoamylases or β-amylases—which hydrolyse starch by releasing maltose from the non-reducing chain ends.

In this respect, Jakubczyk et al. (*Zesz. Nauk. Sck. Gl. Gospod Wiejsk. Warzawie, Technol. Reino-Spozyw*, 1973, 223–235) reported that amyloglucosidase can retard staling of bread baked on wheat flour.

JP-62-79745 and JP-62-79746 state that the use of a β-amylase produced by *Bacillus stearothermophilus* and *Bacillus megaterium*, respectively may be effective in retarding staling of starchy foods, including bread.

EP-A-412,607 discloses a process for the production of a bread product having retarded staling properties by the addition to the dough of a thermostable exoamylase, which is not inactivated before gelatinization. Only amyloglycosidases and β-amylases are listed as suitable exoamylases to be used. The exoamylase is in an amount which is able to modify selectively the crystallisation properties of the amylopectin component during baking by splitting off glucose or maltose from the non-reducing ends of amylose and amylopectin. According to EP-A-412,607, the exoamylase selectively reduces the crystallisation properties of amylopectin, without substantially effecting the crystallisation properties of amylose.

EP-A-494,233 discloses the use of a maltogenic exoamylase to release maltose in the α-configuration and which is not inactivated before gelatinization in a process for the production of a baked product having retarded staling properties. Only a maltogenic α-amylase from Bacillus strain NCIB 11837 is specifically disclosed. Apparently, the maltogenic exoamylase hydrolyses (1→4)-α-glucosidic linkages in starch (and related polysaccharides) by removing α-maltose units from the non-reducing ends of the polysaccharide chains in a stepwise manner.

Thus, the prior art teaches that certain glucogenic exoamylases and maltogenic exoamylases can provide an antistaling effect by selectively reducing the detrimental retrogradation tendencies of amylopectin through shortening of the amylopectin side chains.

Nevertheless, there is still a need to provide different and effective, preferably more effective, means for retarding the detrimental retrogradation, such as retarding the staling, of starch products, in particular baked products, more in particular bread products.

SUMMARY ASPECTS OF THE PRESENT INVENTION

The present invention provides a process for making a starch product that has a retarded detrimental retrogradation property.

The present invention also provides enzymes that are useful in the process of the present invention.

The enzymes of the present invention are amylase enzymes. More in particular, the enzymes of the present invention are non-maltogenic exoamylase enzymes.

It is to be noted that non-maltogenic exoamylases have not hitherto been used to retard the detrimental retrogradation of starch products, let alone to retard staling in baked products.

Thus, according to a first aspect of the present invention there is provided a process for making a starch product comprising adding to a starch medium a non-maltogenic exoamylase that is capable of hydrolysing starch by cleaving off linear maltooligosaccharides, predominantly consisting of from four to eight D-glucopyranosyl units, from the non-reducing ends of the side chains of amylopectin.

Addition of the non-maltogenic exoamylase to the starch medium may occur during and/or after heating of the starch product.

Thus, according to a second aspect of the present invention there is provided a baked product obtained by the process according to the present invention.

Thus, according to a third aspect of the present invention there is provided an improver composition for a dough; wherein the composition comprises a non-maltogenic exoamylase, and at least one further dough ingredient or dough additive.

Thus, according to a fourth aspect of the present invention there is provided the use of a non-maltogenic exoamylase in a starch product to retard the detrimental retrogradation of the starch product.

Thus, according to a fifth aspect of the present invention there is provided a novel non-maltogenic exoamylase.

These and other aspects of the present invention are presented in the acompanying claims. In addition, these and other aspects of the present invention, as well as preferred aspects thereof, are presented and dicussed below.

General Definitions

Thus, the present invention relates to the use of proteins that are capable of retarding the detrimental retrogradation of starch media, in particular starch gels.

In one preferred aspect, the present invention relates to the use of proteins that are capable of retarding the staling of starch.

In another aspect, the present invention relates to the use of proteins that are capable of retarding the detrimental retrogradation of starch media, such as starch gels.

In accordance with the present invention, the term "starch" means starch per se or a component thereof, especially amylopectin.

In accordance with the present invention, the term "starch medium" means any suitable medium comprising starch.

The term "starch product" means any product that contains or is based on or is derived from starch.

Preferably, the starch product contains or is based on or is derived from starch obtained from wheat flour.

The term "wheat flour" as used herein is a synonym for the finely-ground meal of wheat or other grain. Preferably, however, the term means flour obtained from wheat per se and not from another grain. Thus, and unless otherwise expressed, references to "wheat flour" as used herein preferably mean references to wheat flour per se as well as to wheat flour when present in a medium, such as a dough.

A preferred flour is wheat flour or rye flour or mixtures of wheat and rye flour. However, dough comprising flour derived from other types of cereals such as for example from rice, maize, barley, and durra are also contemplated.

Preferably, the starch product is a bakery product.

More preferably, the starch product is a bread product.

Even more preferably, the starch product is a baked farinaceous bread product.

The term "baked farinaceous bread product" is understood to refer to any baked product based on ground cereals and baked on a dough obtainable by mixing flour, water, and a leavening agent under dough forming conditions. It is, however, within the scope of the present invention that further components can be added to the dough mixture.

The term "amylase" is used in its normal sense—e.g. an enzyme that is inter alia capable of catalysing the degradation of starch. In particular they are hydrolases which are capable of cleaving $\alpha$-D-(1$\rightarrow$4) O-glycosidic linkages in starch.

The term "non-maltogenic exoamylase enzyme" means the enzyme does not initially degrade starch to substantial amounts of maltose. In a highly preferred aspect, the term also means the enzyme does not initially degrade starch to substantial amounts of maltose and glucose.

Before the present invention, non-maltogenic exoamylase enzymes had not been suggested for retarding the detrimental retrogradation of starch media, in particular starch gels.

A suitable assay for determining amylase activity in accordance with the present invention is presented later. For convenience, this assay is called the "Amylase Assay Protocol".

Thus, preferably, the term "non-maltogenic exoamylase enzyme" means that the enzyme does not initially degrade starch to substantial amounts of maltose as analysed in accordance with the product determination procedure as described in the "Amylase Assay Protocol" presented herein.

In a preferred aspect, the non-maltogenic exoamylase can be characterised in that if an amount of 0.7 units of said non-maltogenic exoamylase were to incubated for 15 minutes at a temperature of 50° C. at pH 6.0 in 4 ml of an aqueous solution of 10 mg preboiled waxy maize starch per ml buffered solution containing 50 mM 2-(N-morpholino) ethane sulfonic acid and 2 mM calcium chloride then the enzyme would yield hydrolysis product(s) that would consist of one or more linear malto-oligosaccharides of from two to ten D-glucopyranosyl units and optionally glucose; such that at least 60%, preferably at least 70%, more preferably at least 80% and most preferably at least 85% by weight of the said hydrolysis products would consist of linear maltooligosaccharides of from three to ten D-glucopyranosyl units, preferably of linear maltooligosaccharides consisting of from four to eight D-glucopyranosyl units.

For ease of reference, and for the present purposes, the feature of incubating an amount of 0.7 units of the non-maltogenic exoamylase for 15 minutes at a temperature of 50° C. at pH 6.0 in 4 ml of an aqueous solution of 10 mg preboiled waxy maize starch per ml buffered solution containing 50 mM 2-(N-morpholino)ethane sulfonic acid and 2 mM calcium chloride, may be referred to as the "waxy maize starch incubation test".

Thus, alternatively expressed, a preferred non-maltogenic exoamylase is characterised as having the ability in the waxy maize starch incubation test to yield hydrolysis product(s) that would consist of one or more linear malto-oligosaccharides of from two to ten D-glucopyranosyl units and optionally glucose; such that at least 60%, preferably at least 70%, more preferably at least 80% and most preferably at least 85% by weight of the said hydrolysis product(s) would consist of linear maltooligosaccharides of from three to ten D-glucopyranosyl units, preferably of linear maltooligosaccharides consisting of from four to eight D-glucopyranosyl units.

The hydrolysis products in the waxy maize starch incubation test include one or more linear malto-oligosaccharides of from two to ten D-glucopyranosyl units and optionally glucose. The hydrolysis products in the waxy maize starch incubation test may also include other hydrolytic products. Nevertheless, the % weight amounts of linear maltooligosaccharides of from three to ten D-glucopyranosyl units are based on the amount of the hydrolysis product that consists of one or more linear malto-oligosaccharides of from two to ten D-glucopyranosyl units and optionally glucose. In other words, the % weight amounts of linear maltooligosaccharides of from three to ten D-glucopyranosyl units are not based on the amount of hydrolysis products other than one or more linear malto-oligosaccharides of from two to ten D-glucopyranosyl units and glucose.

The hydrolysis products can be analysed by any suitable means. For example, the hydrolysis products may be analysed by anion exchange HPLC using a Dionex PA 100 column with pulsed amperometric detection and with, for example, known linear maltooligosaccharides of from glucose to maltoheptaose as standards.

For ease of reference, and for the present purposes, the feature of analysing the hydrolysis product(s) using anion exchange HPLC using a Dionex PA 100 column with pulsed amperometric detection and with known linear maltooligosaccharides of from glucose to maltoheptaose used as standards, can be referred to as "analysing by anion exchange". Of course, and as just indicated, other analytical techniques would suffice, as well as other specific anion exchange techniques.

Thus, alternatively expressed, a preferred non-maltogenic exoamylase is characterised as having the ability in a waxy maize starch incubation test to yield hydrolysis product(s) that would consist of one or more linear malto-oligosaccharides of from two to ten D-glucopyranosyl units and optionally glucose, said hydrolysis products being capable of being analysed by anion exchange; such that at least 60%, preferably at least 70%, more preferably at least 80% and most preferably at least 85% by weight of the said hydrolysis product(s) would consist of linear maltooligosaccharides of from three to ten D-glucopyranosyl units, preferably of linear maltooligosaccharides consisting of from four to eight D-glucopyranosyl units.

As used herein with respect to the present invention, the term "linear malto-oligosaccharide" is used in the normal sense as meaning 2–10 units of α-D-glucopyranose linked by an α-(1→4) bond.

The term "obtainable from *P. saccharophila*" means that the enzyme need not necessarily be obtained from *P. saccharophila*. Instead, the enzyme could be prepared by use of recombinant DNA techniques.

The term "functional equivalent thereof" in relation to the enzyme being obtainable from *P. saccharophila* means that the functional equivalent could be obtained from other sources. The functionally equivalent enzyme may have a different amino acid sequence but will have non-maltogenic exoamylase activity. The functionally equivalent enzyme may have a different chemical structure and/or formula but will have non-maltogenic exoamylase activity. The functionally equivalent enzyme need not necessarily have exactly the same non-maltogenic exoamylase activity as the non-maltogenic exoamylase enzyme obtained from *P. saccharophila*. For some applications, preferably, the functionally equivalent enzyme has at least the same activity profile as the enzyme obtained from *P. saccharophila*.

The term "obtainable from *Bacillus clausii*" means that the enzyme need not necessarily be obtained from *Bacillus clausii*. Instead, the enzyme could be prepared by use of recombinant DNA techniques.

The term "functional equivalent thereof" in relation to the enzyme being obtainable from *Bacillus clausii* means that the functional equivalent could be obtained from other sources. The functionally equivalent enzyme may have a different amino acid sequence but will have non-maltogenic exoamylase activity. The functionally equivalent enzyme may have a different chemical structure and/or formula but will have non-maltogenic exoamylase activity. The functionally equivalent enzyme need not necessarily have exactly the same non-maltogenic exoamylase activity as the non-maltogenic exoamylase enzyme obtained from *Bacillus clausii*. For some applications, preferably, the functionally equivalent enzyme has at least the same activity profile as the enzyme obtained from *Bacillus clausii* (such as the reactivity profile shown in FIG. 7).

General Comments

The present invention is based on the surprising finding that non-maltogenic exoamylases are highly effective in retarding or reducing detrimental retrogradation, such as staling, in starch products, in particular baked products.

We have found that non-maltogenic exoamylases according to the present invention can be more effective in retarding detrimental retrogradation, such as staling, in bread than the glucogenic and maltogenic exoamylases.

The reduction of detrimental retrogradation can be measured by standard techniques known in the art. By way of example, some techniques are presented later on in the section titled "Assay for the Measurement of Retrogradation".

In our studies, we have found that by incorporating a sufficient amount of activity of a non-maltogenic exoamylase, like for instance a exo-maltotetraohydrolase (EC 3.2.1.60), which has a sufficient thermostability, into a dough there is provided baked products with reduced, in some cases significantly reduced, detrimental retrogradation compared to that of a control bread, such as under storage conditions. In contrast, the reducing effect on detrimental retrogradation of incorporating the same amount of activity of a maltogenic exoamylase with a comparable thermostability to that of the non-maltogenic exoamylase is significantly less. Thus, the anti-retrogradation effect of non-maltogenic exoamylase is more efficient than that of a maltogenic exoamylase. We believe that this difference may be, in part, due to the extent to which the amylopectin side chains are shortened. We also believe that the anti-retrogradation effect may be even more pronounced when using a non-maltogenic exoamylase according to the invention which releases maltoheptaose and/or maltooctaose and/or maltohexose.

In our studies we have also purified and characterised a product-specific amylase active at high pH producing maltohexaose. This amylase was isolated from an alkali-tolerant strain of *Bacillus clausii* BT-21.

Furthermore, we have found that the retardation of detrimental retrogradation that is obtainable by using non-maltogenic exoamylases according to the present invention is dose responsive over a very wide range. This is in contrast to the effect from maltogenic exoamylases, which is rather limited and has a strongly decreasing dose response.

Amylases

In one aspect, the present invention provides the use of certain amylases to prepare starch products, such as bakery products. In this respect, the amylases—which are non-maltogenic exoamylases—retard or reduce the staling properties (i.e. lower the rate of staling) of the starch product, in particular a baked farinaceous bread product.

Preferably, the amylase is in an isolated form and/or in a substantially pure form. Here, the term "isolated" means that the enzyme is not in its natural environment.

As indicated above, the non-maltogenic exoamylase enzyme of the present invention does not initially degrade starch to substantial amounts of maltose.

According to the present invention, the non-maltogenic exoamylase is capable of cleaving off linear maltooligosaccharides, predominantly consisting of from four to eight D-glucopyranosyl units, from the non-reducing ends of the side chains of amylopectin. Non-maltogenic exoamylases having this characteristic and which are suitable for use in the present invention are identified by their ability to hydrolyse gelatinised waxy maize starch in the model system presented in the Amylase Assay Protocol (infra).

When incubated 15 min. under the described conditions in the Amylase Assay Protocol, the non-maltogenic exoamylases which are suitable for use according to the present invention would yield a hydrolysis product(s) that would consist of one or more linear malto-oligosaccharides of from two to ten D-glucopyranosyl units and optionally glucose, such that the product pattern of that hydrolysis product would consist of at least 60%, in particular at least 70%, more preferably at least 80% and most preferably at least 90% by weight of starch hydrolysis degradation products other than maltose and glucose.

For a preferred aspect of the present invention, the non-maltogenic exoamylases which are suitable for use according to the present invention would provide when incubated 15 min. under the described conditions for the waxy maize starch incubation test the said hydrolysis product, such that the hydrolysis product would have a product pattern of at least 60%, in particular at least 70%, more preferably at least 80% and most preferably at least 90% by weight of linear malto-oligosaccharides of from three to ten D-glucopyranosyl units, in particular linear maltooligosaccharides consisting of from four to eight D-glucopyranosyl units.

In a more preferred aspect of the present invention, the said hydrolysis product in said test would have a product pattern of at least 60%, in particular at least 70%, more preferably at least 80% and most preferably at least 85% by weight of linear maltooligosaccharides of 4 or 6 D-glucopyranosyl units.

In a more preferred aspect of the present invention, the said hydrolysis product in said test would have a product pattern of at least 60%, in particular at least 70%, more preferably at least 80% and most preferably at least 85% by weight linear maltooligosaccharides of 4 D-glucopyranosyl units.

In a more preferred aspect of the present invention, the said hydrolysis product in said test would have a product pattern of at least 60%, in particular at least 70%, more preferably at least 80% and most preferably at least 85% by weight of linear maltooligosaccharides of 6 D-glucopyranosyl units.

Preferentially, the non-maltogenic exoamylase does not substantially hydrolyze its primary products to convert them to glucose, maltose and maltotriose. If that were the case, the primary products would compete as substrates with the amylopectin non-reducing chain ends for the enzyme, so that its anti-retrogradation efficiency would be reduced.

Thus, preferentially, the non-maltogenic exoamylase when incubated for 300 min. under conditions similar to the waxy maize starch incubation test but wherein the 15 min. period is extended to 300 min.—as an aside, and for convenience for the present purposes, this modified waxy maize starch incubation test may be called the "extended waxy maize starch incubation test"—would still yield the said hydrolyis product wherein the hydrolysis product would have a product pattern of at least 50%, in particular at least 60%, more preferably at least 70% and most preferably at least 80% by weight of from four to eight D-glucopyranosyl units.

By way of example, a non-maltogenic exoamylase useful in the process of the present invention can be characterised in that it has the ability in a waxy maize starch incubation test to yield hydrolysis product(s) that would consist of one or more linear malto-oligosaccharides of from two to ten D-glucopyranosyl units and optionally glucose; such that at least 60%, preferably at least 70%, more preferably at least 80% and most preferably at least 85% by weight of the said hydrolysis product(s) would consist of linear maltooligosaccharides of from three to ten D-glucopyranosyl units, preferably of linear maltooligosaccharides consisting of from four to eight D-glucopyranosyl units; and wherein the enzyme is obtainable from *P. saccharophila* or is a functional equivalent thereof.

By way of further example, another non-maltogenic exoamylase useful in the process of the present invention can be characterised in that it has the ability in a waxy maize starch incubation test to yield hydrolysis product(s) that would consist of one or more linear malto-oligosaccharides of from two to ten D-glucopyranosyl units and optionally glucose; such that at least 60%, preferably at least 70%, more preferably at least 80% and most preferably at least 85% by weight of the said hydrolysis product(s) would consist of linear maltooligosaccharides of from three to ten D-glucopyranosyl units, preferably of linear maltooligosaccharides consisting of from four to eight D-glucopyranosyl units; wherein the enzyme is obtainable from *Bacillus clausii* or is a functional equivalent thereof; and wherein the enzyme has a molecular weight of about 101,000 Da (as estimated by sodium dodecyl sulphate polyacrylamide electrophoresis) and/or the enzyme has an optimum of activity at pH 9.5 and 55° C.

Preferably, the non-maltogenic exoamylases which are suitable for use according to the present invention are active during baking and hydrolyse starch during and after the gelatinization of the starch granules which starts at temperatures of about 55° C. The more thermostable the non-maltogenic exoamylase is the longer time it can be active and thus the more antistaling effect it will provide. However, during baking above temperatures of about 85° C. the non-maltogenic exoamylase is preferentially gradually inactivated so that there is substantially no activity after the baking process in the final bread. Therefore preferentially the non-maltogenic exoamylases suitable for use according to the present invention have an optimum temperature above 45° C. and below 98° C. when incubated for 15 min. at 40, 45, 50, 55, 60, 65, 70, 75, 80, 85, or 90° C. in a test tube with 4 ml of 10 mg/ml waxy maize starch in 50 mM MES, 2 mM calcium chloride, pH 6.0 prepared as described above and assayed for release of hydrolysis products as described above. Preferably the optimum temperature of the non-maltogenic exoamylase is above 55° C. and below 95° C. and even more preferably it is above 60° C. and below 90° C.

Non-maltogenic exoamylases which may be found to be less thermostable can be improved by using protein engineering to become more thermostable and thus better suited for use according to present the invention. Thus the use of non-maltogenic exoamylases modified to become more thermostable by protein engineering is encompassed by the present invention.

It is known that some non-maltogenic exoamylases can have some degree of endoamylase activity. In some cases, this type of activity may need to be reduced or eliminated since endoamylase activity can possibly negatively effect the quality of the final bread product by producing a sticky or gummy crumb due to the accumulation of branched dextrins.

Thus, in a preferred aspect, the non-maltogenic exoamylase of the present invention will have less than 0.5 endoamylase units (EAU) per unit of exoamylase activity.

Preferably the non-maltogenic exoamylases which are suitable for use according to the present invention have less than 0.05 EAU per unit of exoamylase activity and more preferably less than 0.01 EAU per unit of exoamylase activity.

The endoamylase units can be determined by use of the Endoamylase Assay Protocol presented below.

Examples of non-maltogenic exoamylases suitable for use according to the present invention include exo-maltotetraohydrolase (E.C.3.2.1.60), exo-maltopentaohydrolase and exo-maltohexaohydrolase (E.C.3.2.1.98) which hydrolyze 1,4α-glucosidic linkages in amylaceous polysaccharides so as to remove successive residues of maltotetraose, maltopentaose or maltohexaose, respectively, from the non-reducing chain ends. Examples are exo-maltotetra-hydrolases of *Pseudomonas saccharophila* and *P. stutzeri* (EP-0 298 645 B1), exo-maltopentahydrolases of an alkaliphilic Gram-positive bacterium (U.S. Pat. No. 5,204,254) and of Pseudomonas sp. (Shida et al., *Biosci. Biotechnol. Biochem.*, 1992, 56, 76–80) and exo-maltohexaohydrolases of Bacillus sp. #707 (Tsukamoto et al., *Biochem. Biophys. Res. Commun.*, 1988, 151, 25–31), *B. circulans* F2 (Taniguchi, *ACS Symp.*, 1991, Ser. 458, 111–124) and *Aerobacter aerogenes* (Kainuma et al., *Biochim. Biophys. Acta,* 1975, 410, 333–346).

Another example of a non-maltogenic exoamylase suitable for use according to the invention is the exoamylase from an alkalophilic Bacillus strain, GM8901 (28). This is a non-maltogenic exoamylase which produces maltotetraose as well as maltopentaose and maltohexaose from starch.

Furthermore, non-maltogenic exoamylases suitable for use according to the present invention also include exo-maltoheptaohydrolase or exo-maltooctaohydrolase which hydrolyze 1,4-α-glucosidic linkages in amylaceous polysaccharides so as to remove residues of maltoheptaose or maltooctaose, respectively, from the non-reducing chain ends. Exo-maltoheptaohydrolase and exo-maltooctaohydrolase can be found either by screening wild type strains or can be developed from other amylolytic enzymes by protein engineering. Thus, non-maltogenic exoamylases developed by protein engineering from other amylolytic enzymes to become non-maltogenic exoamylases are also suitable for use in the present invention.

Novel Amylase

In one aspect, the present invention also provides a novel amylase that is suitable for preparing starch products according to the present invention, such as bakery products. The novel amylase of the present invention is a non-maltogenic exoamylase. In our studies, we have chararacterised this new amylase that is suitable for the preparation of foodstuffs, in particular doughs for use in the preparation of bakery products.

Thus, the present invention also provides a non-maltogenic exoamylase, wherein the non-maltogenic exoamylase is further characterised in that it has the ability in a waxy maize starch incubation test to yield hydrolysis product(s) that would consist of one or more linear malto-oligosaccharides of from two to ten D-glucopyranosyl units and optionally glucose; such that at least 60%, preferably at least 70%, more preferably at least 80% and most preferably at least 85% by weight of the said hydrolysis product(s) would consist of linear maltooligosaccharides of from three to ten D-glucopyranosyl units, preferably of linear maltooligosaccharides consisting of from four to eight D-glucopyranosyl units; wherein the enzyme is obtainable from *Bacillus clausii* or is a functional equivalent thereof; and wherein the enzyme has a molecular weight of about 101,000 Da (as estimated by sodium dodecyl sulphate polyacrylamide electrophoresis) and/or the enzyme has an optimum of activity at pH 9.5 and 55° C.

Preferably, the amylase is in an isolated form and/or in a substantially pure form. Here, the term "isolated" means that the enzyme is not in its natural environment.

Antibodies

The enzymes of present invention can also be used to generate antibodies—such as by use of standard techniques. Thus, antibodies to each enzyme according to the present invention may be raised. The or each antibody can be used to screen for other suitable amylase enzymes according to the present invention. In addition, the or each antibody may be used to isolate amounts of the enzyme of the present invention.

For the production of antibodies, various hosts including goats, rabbits, rats, mice, etc. may be immunized by injection with the inhibitor or any portion, variant, homologue, fragment or derivative thereof or oligopeptide which retains immunogenic properties. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. BCG (*Bacilli Calmette-Guerin*) and *Corynebacterium parvum* are potentially useful human adjuvants which may be employed.

Monoclonal antibodies to the enzyme may be even prepared using any technique which provides for the production of antibody molecules by continuous cell lines in culture. These include, but are not limited to, the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) Monoclonal Antibodies and Cancer Therapy, Alan R Liss Inc, pp 77–96). In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,779) can be adapted to produce inhibitor specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Improver Composition

As indicated, one aspect of the present invention relates to an improver composition for a starch product, in particular a dough and/or a baked farinaceous bread product made from the dough.

The improver composition comprises a non-maltogenic exoamylase according to the present invention and at least one further dough ingredient or dough additive.

According to the present invention the further dough ingredient or dough additive can be any of the dough ingredients and dough additives which are described above.

Expediently, the improver composition is a dry pulverulent composition comprising the non-maltogenic exoamylase according to the invention admixed with at least one further ingredient or additive. However, the improver composition may also be a liquid preparation comprising the non-maltogenic exoamylase according to the invention and at least one further ingredient or additive dissolved or dispersed in water or other liquid. It will be understood that the amount of enzyme activity in the improver composition will depend on the amounts and types of the further ingredients and additives which form part of the improver composition.

Optionally, the improver composition may be in the form of a complete mixture, a so-called pre-mixture, containing all of the dry ingredients and additives for making a particular baked product.

Preparation of Starch Products

In accordance with one aspect of the present invention, the process comprises forming the starch product by adding a suitable non-maltogenic exoamylase enzyme, such as one of the novel non-maltogenic exoamylase enzymes presented herein, to a starch medium.

If the starch medium is a dough, then the dough is prepared by mixing together flour, water, the non-maltogenic exoamylase according to the invention and other possible ingredients and additives.

By way of further example, if the starch product is a baked farinaceous bread product (which is a highly preferred embodiment), then the process comprises mixing—in any suitable order—flour, water, and a leavening agent under dough forming conditions and further adding a suitable non-maltogenic exoamylase enzyme.

The leavening agent may be a chemical leavening agent such as sodium bicarbonate or any strain of *Saccharomyces cerevisiae* (Baker's Yeast).

The non-maltogenic exoamylase can be added together with any dough ingredient including the water or dough ingredient mixture or with any additive or additive mixture.

The dough can be prepared by any conventional dough preparation method common in the baking industry or in any other industry making flour dough based products.

Baking of farinaceous bread products such as for example white bread, bread made from bolted rye flour and wheat flour, rolls and the like is typically accomplished by baking the bread dough at oven temperatures in the range of from 180 to 250° C. for about 15 to 60 minutes. During the baking process a steep temperature gradient (200→120° C.) is prevailing in the outer dough layers where the characteristic crust of the baked product is developed. However, owing to heat consumption due to steam generation, the temperature in the crumb is only close to 100° C. at the end of the baking process.

The non-maltogenic exoamylase can be added as a liquid preparation or as a dry pulverulent composition either comprising the enzyme as the sole active component or in admixture with one or more additional dough ingredient or dough additive.

In order to improve further the properties of the baked product and impart distinctive qualities to the baked product further dough ingredients and/or dough additives may be incorporated into the dough. Typically, such further added components may include dough ingredients such as salt, grains, fats and oils, sugar, dietary fibre substances, milk powder, gluten and dough additives such as emulsifiers, other enzymes, hydrocolloids, flavouring agents, oxidising agents, minerals and vitamins.

The emulsifiers are useful as dough strengtheners and crumb softeners. As dough strengtheners, the emulsifiers can provide tolerance with regard to resting time and tolerance to shock during the proofing. Furthermore, dough strengtheners will improve the tolerance of a given dough to variations in the fermentation time. Most dough strengtheners also improve on the oven spring which means the increase in volume from the proofed to the baked goods. Lastly, dough strengtheners will emulsify any fats present in the recipe mixture.

The crumb softening, which is mainly a characteristic of the monoglycerides, is attributed to an interaction between the emulsifier and the amylose fraction of the starch leading to formation of insoluble inclusion complexes with the amylose which will not recrystallize upon cooling and which will not therefore contribute to firmness of the bread crumb.

Suitable emulsifiers which may be used as further dough additives include lecithin, polyoxyethylene stearat, mono- and diglycerides of edible fatty acids, acetic acid esters of mono- and diglycerides of edible fatty acids, lactic acid esters of mono- and diglycerides of edible fatty acids, citric acid esters of mono- and diglycerides of edible fatty acids, diacetyl tartaric acid esters of mono- and diglycerides of edible fatty acids, sucrose esters of edible fatty acids, sodium stearoyl-2-lactylate, and calcium stearoyl-2-lactylate.

Other enzymes which are useful as further dough additives include as examples oxidoreductases, such as glucose oxidase, hexose oxidase, and ascorbate oxidase, hydrolases, such as lipases and esterases as well as glycosidases like α-amylase, pullulanase, and xylanase. Oxidoreductases, such as for example glucose oxidase and hexose oxidase, can be used for dough strengthening and control of volume of the baked products and xylanases and other hemicellulases may be added to improve dough handling properties, crumb softness and bread volume. Lipases are useful as dough strengtheners and crumb softeners and α-amylases and other amylolytic enzymes may be incorporated into the dough to control bread volume and further reduce crumb firmness.

The amount of the non-maltogenic exoamylase according to the present invention that is added is normally in an amount which results in the presence in the finished dough of 50 to 100,000 units per kg of flour, preferably 100 to 50,000 units per kg of flour. In useful embodiments of the present invention, the amount is in the range of 200 to 20,000 units per kg of flour.

In the present context, 1 unit of the non-maltogenic exoamylase is defined as the amount of enzyme which releases hydrolysis products equivalent to 1 $\mu$mol of reducing sugar per min. when incubated at 50° C. in a test tube with 4 ml of 10 mg/ml waxy maize starch in 50 mM MES, 2 mM calcium chloride, pH 6.0 as described hereinafter.

Foodstuffs Prepared with Amylases

The present invention provides suitable amylases for use in the manufacture of a foodstuff. Typical foodstuffs, which also include animal feed, include dairy products, meat products, poultry products, fish products and bakery products.

Preferably, the foodstuff is a bakery product, such as the bakery products described above. Typical bakery (baked) products incorporated within the scope of the present invention include bread—such as loaves, rolls, buns, pizza bases etc.—pretzels, tortillas, cakes, cookies, biscuits, krackers etc.

Amylase Assay Protocol

The following system is used to characterize non-maltogenic exoamylases which are suitable for use according to the present invention.

By way of initial background information, waxy maize amylopectin (obtainable as WAXILYS 200 from Roquette, France) is a starch with a very high amylopectin content (above 90%).

20 mg/ml of waxy maize starch is boiled for 3 min. in a buffer of 50 mM MES (2-(N-morpholino)ethanesulfonic acid), 2 mM calcium chloride, pH 6.0 and subsequently incubated at 50° C. and used within half an hour.

One unit of the non-maltogenic exoamylase is defined as the amount of enzyme which releases hydrolysis products equivalent to 1 $\mu$mol of reducing sugar per min. when incubated at 50° C. in a test tube with 4 ml of 10 mg/ml waxy maize starch in 50 mM MES, 2 mM calcium chloride, pH 6.0 prepared as described above.

Reducing sugars are measured using maltose as standard and using the dinitrosalicylic acid method of Bernfeld, *Methods Enzymol.*, (1954), 1, 149–158 or another method known in the art for quantifying reducing sugars.

The hydrolysis product pattern of the non-maltogenic exoamylase is determined by incubating 0.7 units of non-maltogenic exoamylase for in a test tube with 4 ml of 10 mg/ml waxy maize starch in the buffer prepared as described above. The reaction is stopped by immersing the test tube for 3 min. in a boiling water bath.

The hydrolysis products are analyzed and quantified by anion exchange HPLC using a Dionex PA 100 column with sodium acetate, sodium hydroxide and water as eluents, with pulsed amperometric detection and with known linear maltooligo-saccharides of from glucose to maltoheptaose as standards. The response factor used for maltooctaose to maltodecaose is the response factor found for maltoheptaose.

Endoamylase Assay Protocol 0.75 ml of enzyme solution is incubated with 6.75 ml of 0.5% (w/v) of AZCL-amylose (azurine cross-linked amylose available from Megazyme, Ireland) in 50 mM MES (2-(N-morpholino)ethanesulfonic acid), 2 mM calcium chloride, pH 6.0 at 50° C. After 5, 10, 15, 20 and 25 minutes, respectively 1.0 ml of reaction mix is transferred to 4.0 ml of stop solution consisting of 4% (w/v) TRIS (Tris(hydroxymethyl)aminomethane).

The stopped sample is filtered through a Whatman No. 1 filter and its optical density at 590 nm is measured against distilled water. The enzyme solution assayed should be diluted so that the optical density obtained is a linear function of time. The slope of the line for optical density versus time is used to calculate the endoamylase activity relative to the standard GRINDAMYL™ A1000 (available from Danisco Ingredients), which is defined to have 1000 endoamylase units (EAU) per g.

Assays for Measurement of Retrogradation (inc. Staling)

For evaluation of the antistaling effect of the non-maltogenic exoamylase of the present invention, the crumb firmness can be measured 1, 3 and 7 days after baking by means of an Instron 4301 Universal Food Texture Analyzer or similar equipment known in the art.

Another method used traditionally in the art and which is used to evaluate the effect on starch retrogradation of a non-maltogenic exoamylase according to the present invention is based on DSC (differential scanning calorimetry). Hereby the melting enthalpy of retrograded amylopectin in bread crumb or crumb from a model system dough baked with or without enzymes (control) is measured. The DSC equipment applied in the described examples is a Mettler-Toledo DSC 820 run with a temperature gradient of 10° C. per min. from 20 to 95° C. For preparation of the samples 10–20 mg of crumb are weighed and transferred into Mettler-Toledo aluminium pans which then are hermetically sealed.

The model system doughs used in the described examples contain standard wheat flour and optimal amounts of water or buffer with or without the non-maltogenic exoamylase according to the present invention. They are mixed in a 10 or 50 g Brabender Farinograph for 6 or 7 min., respectively. Samples of the doughs are placed in glass test tubes (15*0.8 cm) with a lid. These test tubes are subjected to a baking process in a water bath starting with 30 min. incubation at 33° C. followed by heating from 33 to 95° C. with a gradient of 1.1° C. per min. and finally a 5 min. incubation at 95° C. Subsequently, the tubes are stored in a thermostat at 20° C. prior to DSC analysis.

Summary

In summary the present invention is based on the surprising finding that non-maltogenic exoamylases—which hydrolyse starch by cleaving off linear maltooligosaccharides in the range of four to eight D-glucopyranosyl units from the non-reducing chain ends of amylopectin and which preferably have a sufficient degree of thermostability—are highly effective in retarding or reducing detrimental retrogradation in baked products.

Deposits

The following sample was deposited in accordance with the Budapest Treaty at the recognised depositary DSMZ (Deutsche Sammlung von Mikrooganismen und Zellkulturen GmbH of Mascheroder Weg 1b, D-38124 Braunschweig) on Mar. 12 1999:

BT-21 DSM number DSM 12731

The present invention also encompasses sequences derivable and/or expressable from those deposits and embodiments comprising the same, as well as active fragments thereof.

INTRODUCTION TO THE EXAMPLES SECTION AND THE FIGURES

Brief Description of the Drawings:

The present invention will now be described, by way of example only, with reference to the accompanying drawings in which.

Figure 1:
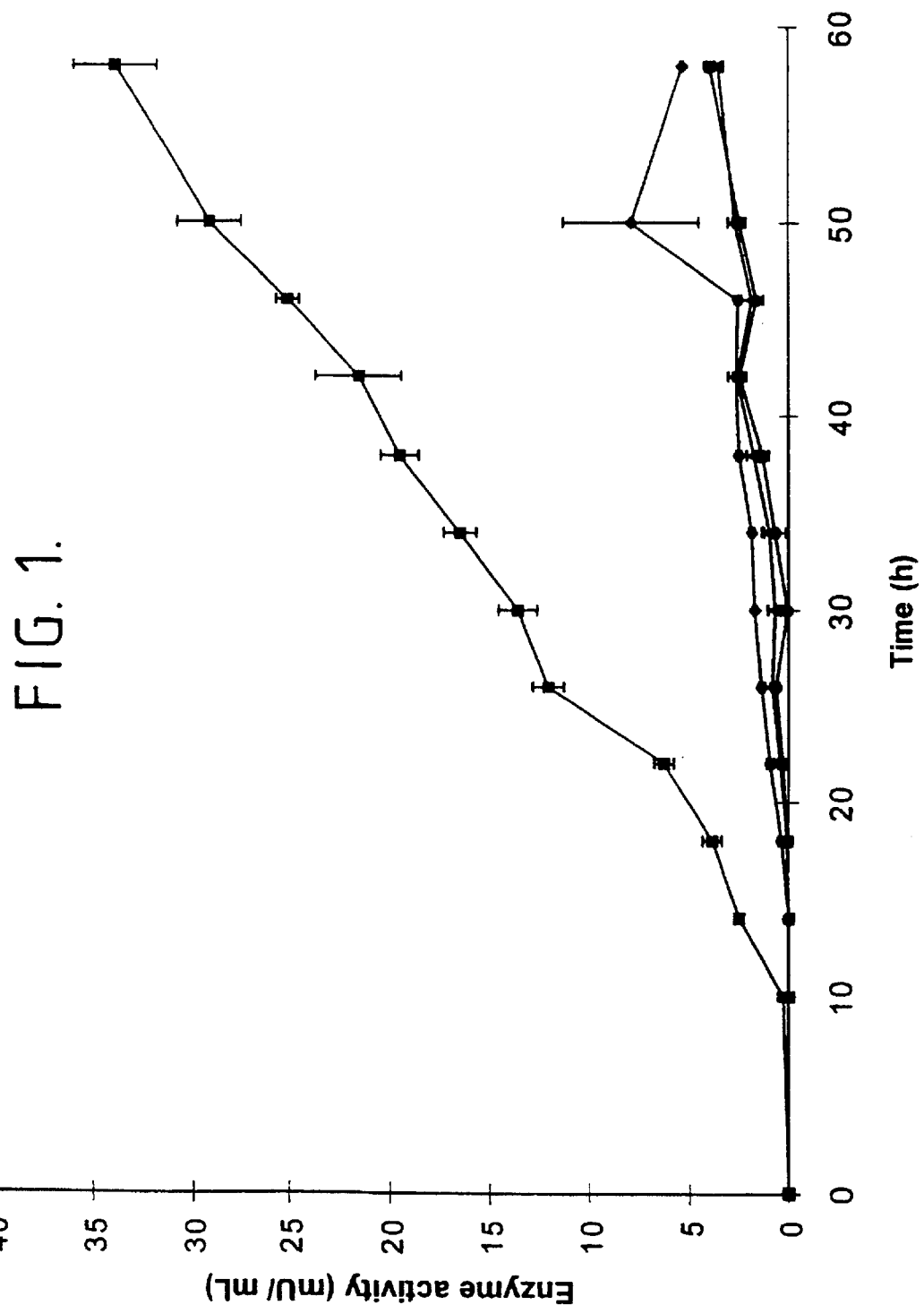
FIG. 1 shows a graph.

In more detail:

FIG. 1. Extracellular amylolytic activity (mU/mL) in liquid cultures of *B. clausii* BT-21 cultured in 2% starch substrates at 45° C. ♦ soluble starch, ● amylopectin, ♦ corn starch, ■ whole brown rice. Bars indicate the standard deviation.

Figure 2:
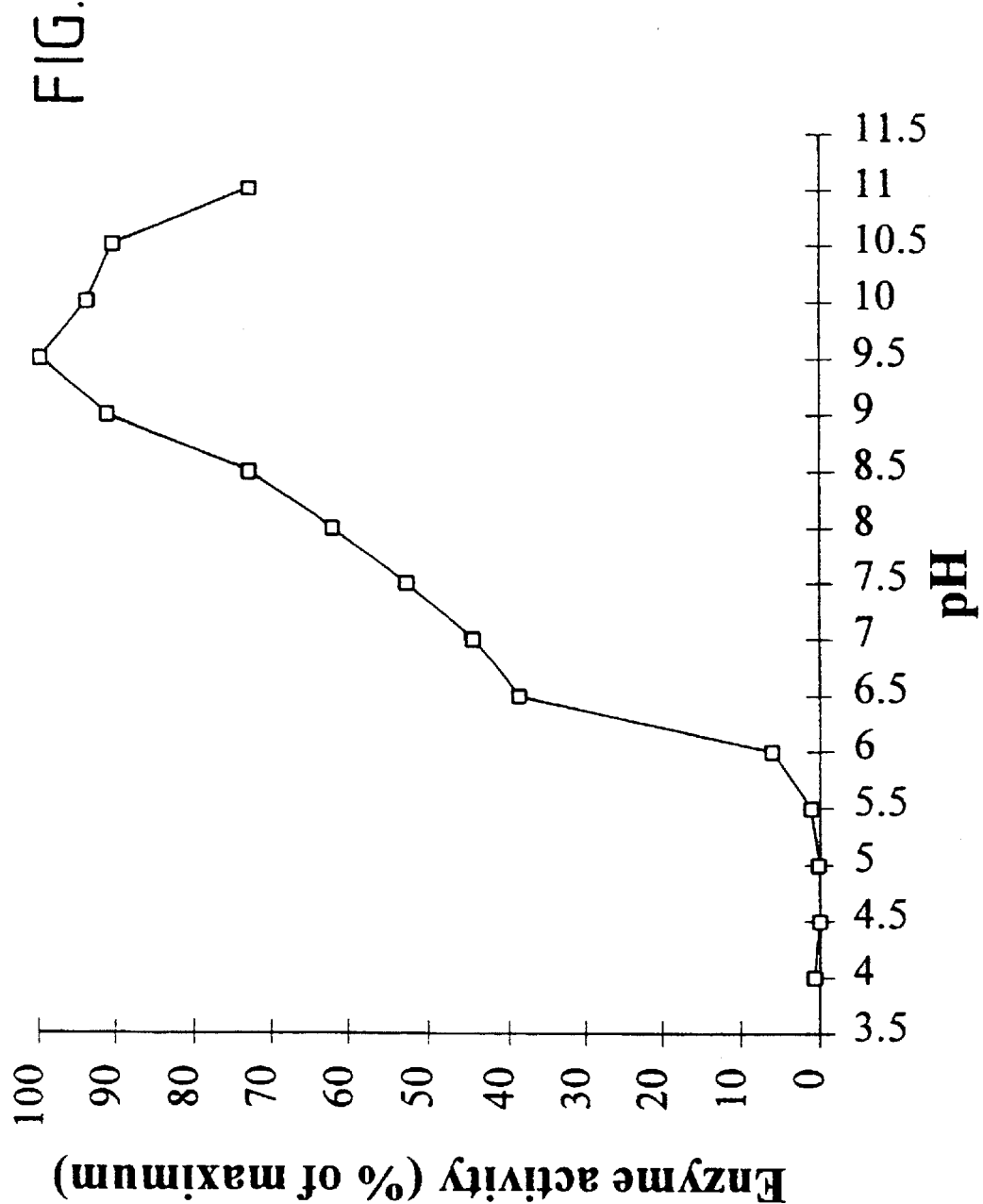
FIG. 2 shows a graph.

FIG. 2. Effect of pH on the activity of the product-specific amylase. Effect of pH at 55° C.

Figure 3:
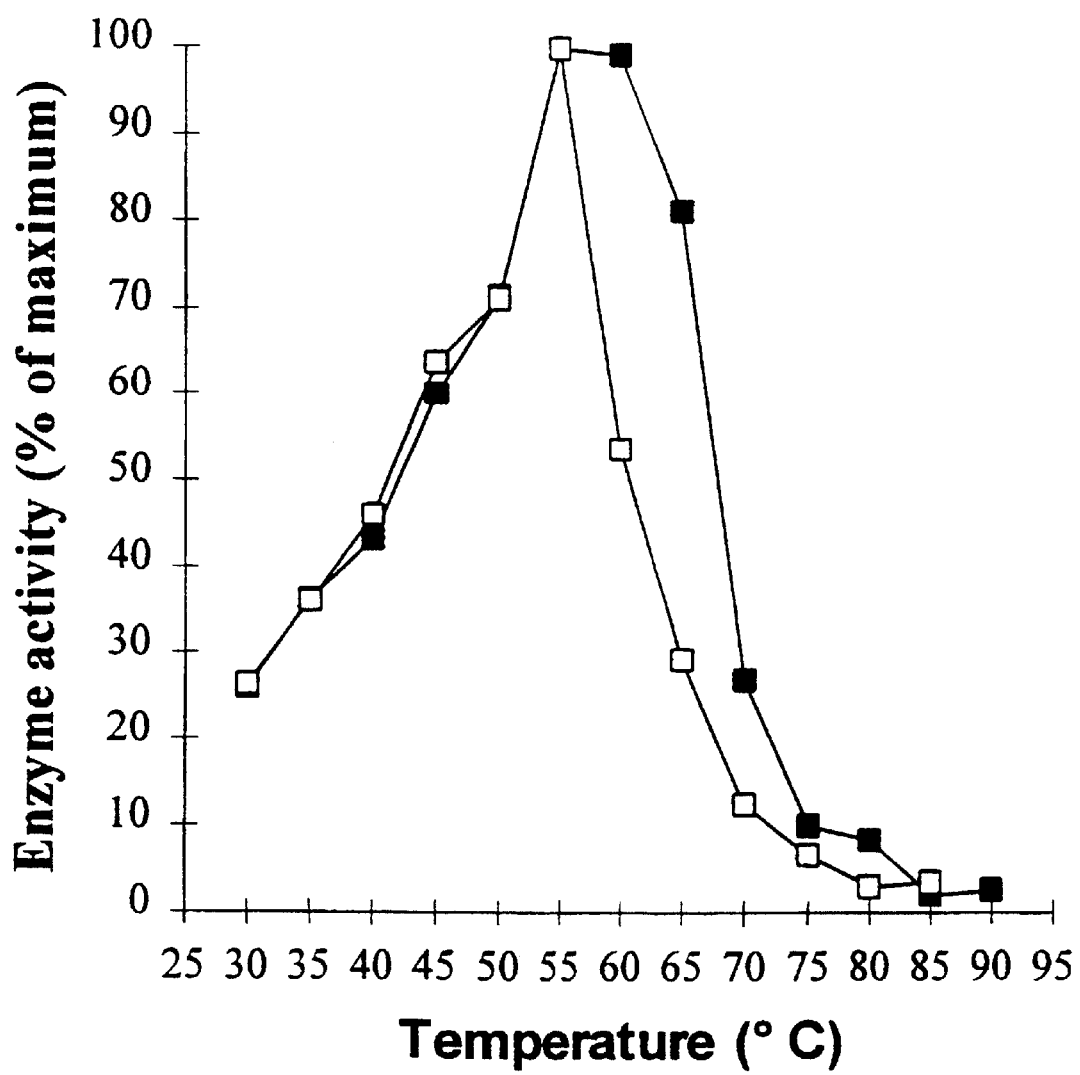
FIG. 3 shows a graph.

FIG. 3. Effect of temperature on the activity of the product-specific amylase. Effect of temperature at pH 9.5 ■ with 5 mM $CaCl_2$ □ without $CaCl_2$.

Figure 4:
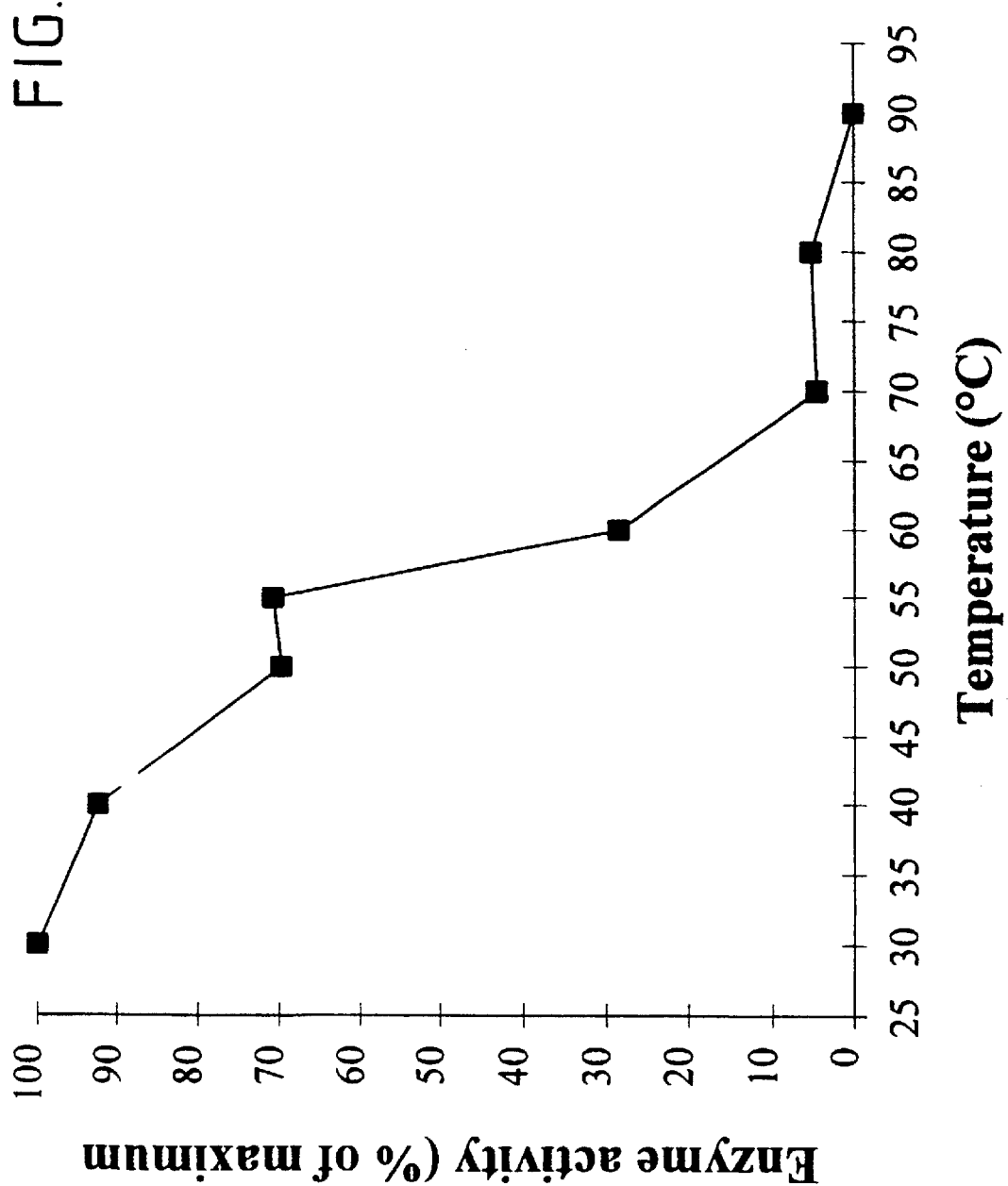
FIG. 4 shows a graph.

FIG. 4. Thermostability tested as residual activity of the product-specific amylase after incubation at increasing temperatures at pH 9.5 with 5 mM $CaCl_2$.

Figure 5:
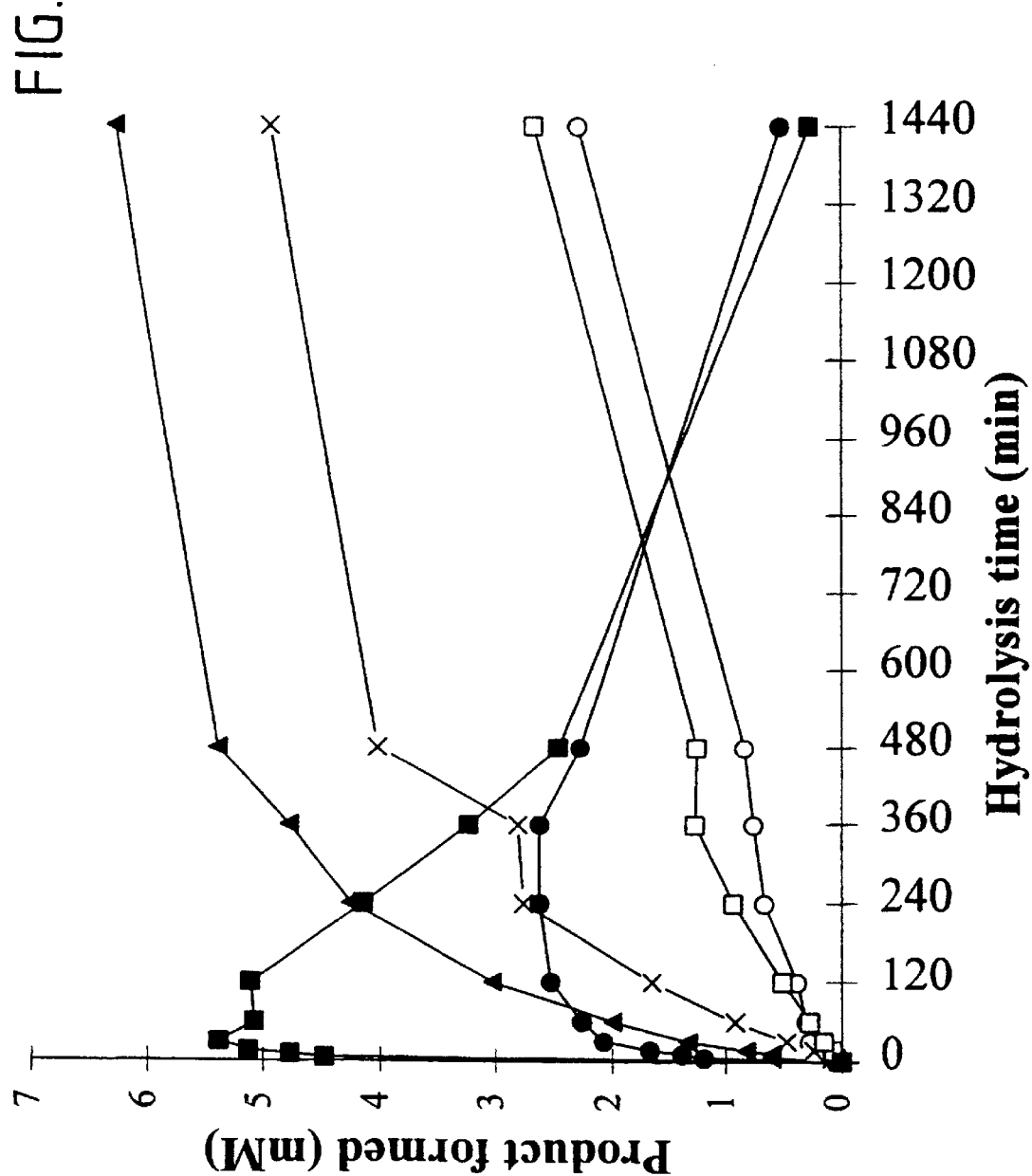
FIG. 5 shows a graph.

FIG. 5. Products (in mM) formed by incubating the product-specific amylase (505 mU/mL) with 1% soluble starch and 5 mM $CaCl_2$ at 55° C. and pH 9.5. ○ glucose, x maltose, □ maltotriose, ▲ maltotetraose, ● maltopentaose, ■ maltohexaose.

Figure 6:
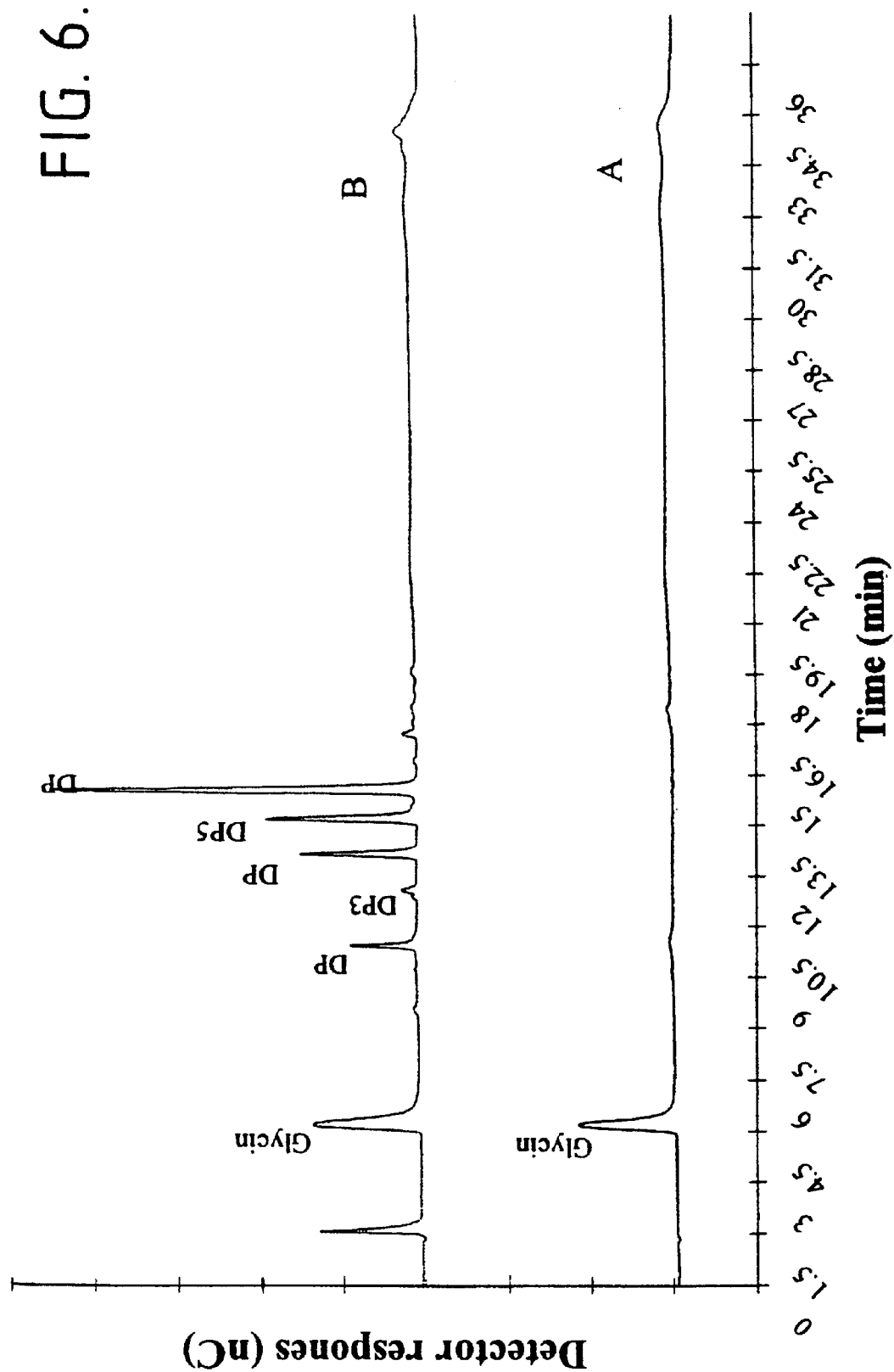
FIG. 6 shows a trace.

FIG. 6. HPAEC-PAD trace obtained by incubating the product-specific amylase (505 mU/mL) with 1% soluble starch at pH 9.5 and 55° C. A) Soluble starch without enzyme, B) Incubation with enzyme for 30 min.

Figure 7:
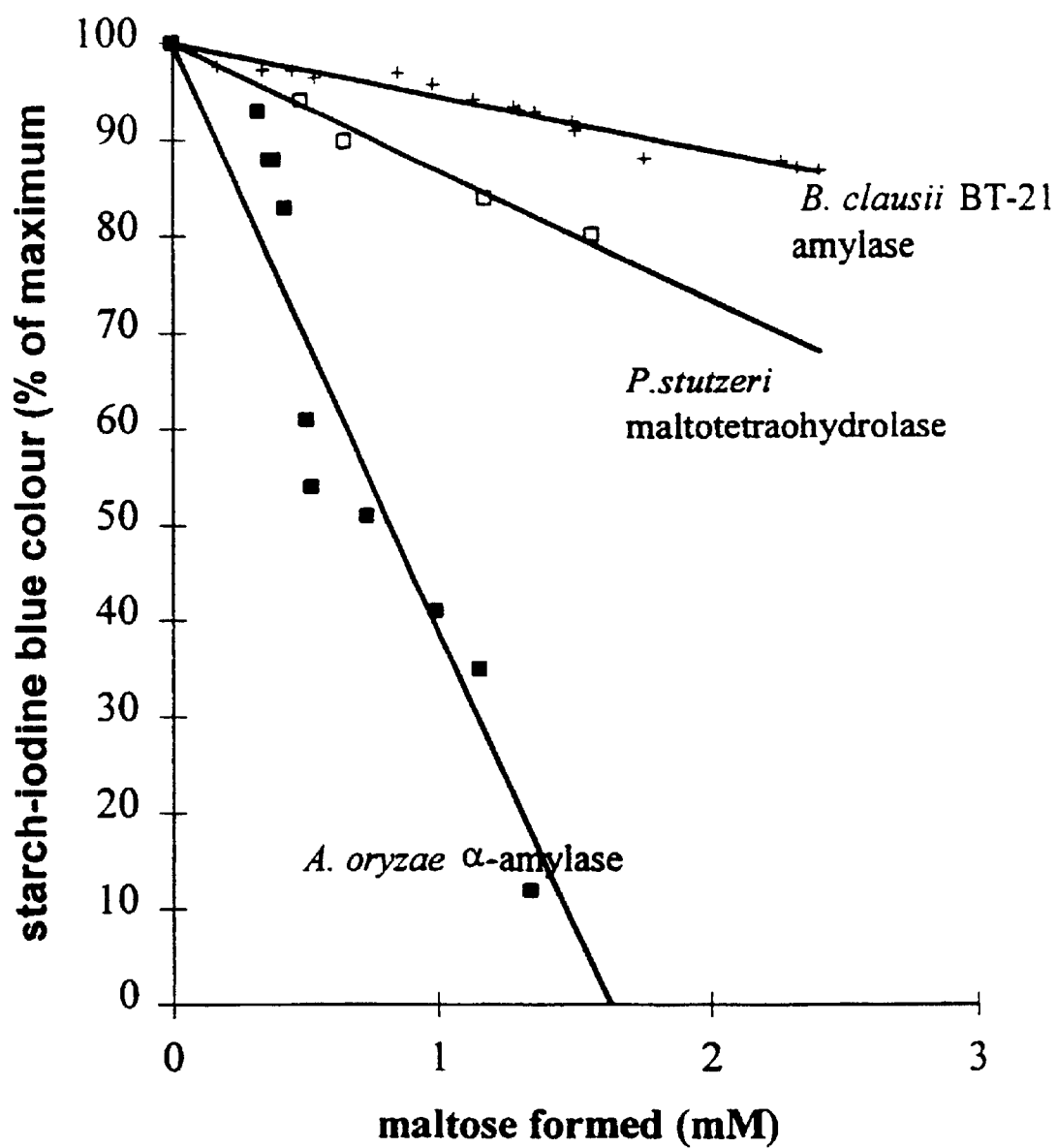
FIG. 7 shows a graph.

FIG. 7. Determination of endo-and exo-activity of *B. clausii* BT-21 product-specific amylase compared to amylases of known starch cleavage action. The blue colour formation (% of maximum) is plotted against the production of mM maltose. The slope of the curves indicate the prevalence of endo- or exo-activity

EXAMPLE—SECTION A

Example 1

Fermentation and Production of *Pseudomonas saccharophila* Non-maltogenic Exoamylase 1.1 Production

*P. saccharophila* strain IAM No. 1544 was obtained from the IAM Culture Collection, Inst. of Molecular and Cellular Biosciences, University of Tokyo, Japan.

Fermentation of the strain was performed in an Applikon ADI 3 liter bioreactor with 2 liter of working volume and under the following conditions:

| | |
|---|---|
| Temperature: | 30° C. |
| Stirring rate: | 1000 rpm |
| Aeration: | 1 volume air per volume medium per minute |
| pH: | constant pH 7.4 by adjustment with 2 M sodium hydroxide and 10% (w/v) hydrochloric acid |

| Medium: | Bacto Tryptone | 20 g/l |
| --- | --- | --- |
| | Bacto Yeast extract | 20 g/l |
| | Starch | 20 g/l |
| | Na$_2$HPO$_4$ · 2H$_2$O | 5.6 g/l |
| | KH$_2$PO$_4$ | 1.5 g/l |

After 1 day of fermentation the fermentation broth was centrifuged and filtered to remove the cells. The activity of non-maltogenic exoamylase in the cell free broth was 5 units per ml determined as described above.

Purification of *P. saccharophila* Non-maltogenic Exoamylase

*P. saccharophila* non-maltogenic exoamylase was partially purified by hydrophobic interaction chromatography using a 150 ml Phenyl Sepharose FF low sub column (Pharmacia, Sweden) equilibrated with A-buffer being 200 mM sodium sulfate, 50 mM triethanolamine, 2 mM calcium chloride, pH 7.2. Filtered fermentation broth (500 ml) was adjusted to 200 mM sodium sulfate and pH 7.2 and loaded onto the column. The non-maltogenic exoamylase was eluted with a linearly decreasing gradient of sodium sulfate in A-buffer. The fractions containing exoamylase activity were pooled.

The pooled fractions were diluted three times with water and further purified by anion-exchange chromatography on a 150 ml Q-Sepharose FF (Pharmacia) column equilibrated with A-buffer being 50 mM triethanolamine, 5 mM calcium chloride, pH 7.5. The non-maltogenic exoamylase was eluted with a linear gradient of 0 to 1 M sodium chloride in A-buffer. The fractions containing exoamylase activity were pooled. This partially purified preparation was used for the tests described below. It had an activity of 14.7 units per ml and only one band of amylase activity when tested in a polyacrylamide gel electrophoresis system stained for amylase activity.

1.3 Characterization of *P. saccheraphila* Non-maltogenic Exoamylase

By way of introduction, the DNA sequence for the gene encoding *P. saccharophila* exo-amylase (which we call PS4) has been published by Zhou et al (Zhou JH, Baba T, Takano T, Kobayashi S, Arai Y (1989) FEBS Lett 1989 September 11;255(1):37–41 "Nucleotide sequence of the maltotetrahydrolase gene from *Pseudomonas saccharophila*.". In addition, the DNA sequence can be accessed in GenBank with accession number X16732.

We have now determined the MW of the purified PS4 enzyme by mass spectrometry (MALDI-TOFF) to be 57500±500 D which is in accordance with the theoretical MW of 57741 D derived from the sequence.

The optimum temperature and pH of PS4 are 45° C. and pH 6.5 according to Zhou et al (Zhou J H, Baba T, Takano T. Kobayashi S, Arai Y (1992) Carbohydr Res 1992 January;223:255–61 "Properties of the enzyme expressed by the *Pseudomonas saccharophila* maltotetraohydrolase gene (mta) in *Escherichia coli*.")

The hydrolysis pattern of the non-maltogenic exoamylase was determined by analyzing the hydrolysis products generated by incubating 0.7 units of partially purified non-maltogenic exoamylase for 15 or 300 min. at 50° C. in a test tube with 4 ml of 10 mg/ml waxy maize starch as described above.

The patterns of hydrolysis products detected after 15 min. and 300 min. are shown in Table 1 and indicate that *P. saccharophila* produces a non-maltogenic exoamylase as defined in the present invention and that this enzyme releases maltotetraose as the predominant product accounting for 85.8 wt % and 93.0 wt % after 15 and 300 min. hydrolysis, respectively.

TABLE 1

Hydrolysis products of glucose to maltodecaose of *P. saccharophila* non-maltogenic exoamylase

| Time | DP | 1 | 2 | 3 | 4 | 5 | 6 | 7 | 8 | 9 | 10 | Total |
| --- | --- | --- | --- | --- | --- | --- | --- | --- | --- | --- | --- | --- |
| 15 min. | µg/ml | 1 | 13 | 6 | 1609 | 13 | 29 | 40 | 70 | 51 | 43 | 1875 |
| 15 min. | % | 0.0 | 0.7 | 0.3 | 85.8 | 0.7 | 1.5 | 2.1 | 3.7 | 2.7 | 2.3 | 99.8 |
| 300 min. | µg/ml | 14 | 149 | 135 | 5354 | 81 | 6 | 4 | 12 | 0 | 0 | 5756 |
| 300 min. | % | 0.3 | 2.6 | 2.3 | 93.0 | 1.4 | 0.1 | 0.1 | 0.2 | 0.0 | 0.0 | 100.0 |

Example 2

Baking Test of *P. saccharophila* Non-maltogenic Exoamylase

A baking test was set up to test the antifirming effect of *P. saccharophila* non-maltogenic exoamylase. A recipe for Danish Toast Bread was used. It contains flour (2000 g), dry yeast (30 g), sugar (30 g), salt (30 g) and water (approximately 1200 g corresponding to a dough consistency of 400 Brabender Units (BU)+60 g of additional water to compensate for the dry yeast used) are mixed in a Hobart mixer (model A-200) for 2 minutes at slow speed and for 12 minutes at high speed. The dough temperature is 26° C. at the end of mixing. The dough is rested for 10 minutes at 30° C. after which the dough is divided in dough pieces of 750 g. The dough pieces rest for 5 minutes in a proofing cabinet at a temperature of 33° C. and a relative humidity of 85%. The dough pieces are then moulded on Glimek moulder (type LR-67) with the following settings 1:4, 2:2, 3:14 and 4:12, after which the moulded dough pieces are transferred to baking tins and proofed in a proofing cabinet for 50 minutes at a temperature of 33° C. and a relative humidity of 85%. Finally, the proofed dough pieces are baked for 40 minutes at a temperature of 220° C., with 10 seconds steam, in a Wachtel oven (model AE 416/38 COM).

A partially purified preparation of *P. saccharophila* non-maltogenic exoamylase was added to the dough dosed at 1470 units per kg of flour. After baking the breads with or without the non-maltogenic exoamylase were cooled to 20° C. and thereafter stored at 20° C. in plastic bags. Firmness was determined by means of an Instron 4301 Universal Food Texture Analyzer on day 3 and day 7 after baking as the mean of 10 slices of one bread for day 3 and the mean of 2 breads with 10 slices per bread measured for day. Table 2 shows that a lower firmness in the breads with enzyme added was observed for both days.

TABLE 2

Antifirming effect of *P. saccharophila* non-maltogenic exoamylase

| Treatment | Firmness day 3 | Firmness day 7 |
|---|---|---|
| Control | 49 | 71 |
| PS4 | 43 | 59 |

Table 3 shows that for day 7 the antifirming effect of the *P. saccharophila* non-maltogenic exoamylase is statistically significant on the 95% confidence level.

TABLE 3

Statistical analysis of the antifirming effect of *P. saccharophila* non-maltogenic exoamylase ANOVA Table for Firmness day 7 by Enzyme
Analysis of Variance

| Source | Sum of Squares | Df | Mean square | F-Ratio | P-Value |
|---|---|---|---|---|---|
| Between groups | 144,0 | 1 | 144,0 | 72,00 | 0,0136 |
| Within groups | 4,0 | 2 | 2,0 | | |
| Total (Corr.) | 148,0 | 3 | | | |

The StatAdvisor

The ANOVA table decomposes the variance of Firmness day 7 into two components: a between-group component and a within-group component. The F-ratio, which in this case equals 72,0, is a ratio of the between-group estimate to the within-group estimate. Since the P-value of the F-test is less than 0,05, there is a statistically significant difference between the mean Firmness day 7 from one level of Enzyme to another at the 95,0% confidence level. To determine which means are significantly different from which others, select Multiple Range Tests from the list of Tabular Options.

Example 3

The following describes our cloning and expression of the mta gene encoding non-maltogenic exoamylase from *Pseudomonas saccharophila* in *Escherichia coli* MC1061.

In this respect, *P. saccharophila* IAM 1520 was grown in 2 ml LB medium and cells were harvested by centrifugation 10 min 20.000×g. Total DNA was isolated using a slightly modified miniprep protocol. The cells were resuspended in 300 μl resuspension buffer (50 mM Tris-HCl, pH 8.0; 10 mM EDTA; 100 μg/ml RNase A) after which the cells were disrupted using a Fastprep FP120 (BIO101; California). Following disruption, 300 μl lysis buffer (200 mM NaOH; 1% SDS) and 300 μl neutralization buffer (3.0 M potassium acetate, pH 5.5) were added. After centrifugation at 20,000×g for 15 min at 4° C., the supernatant was collected and 0.6 volumes isopropanol was added. The DNA was precipitated by centrifugation at 20,000×g for 30 min at 4° C., washed with 70% ethanol, and redissolved in 100 μl TE (10 mM Tris-HCl, pH 8.0, 1 mM EDTA).

For PCR amplification 4 different primers were designed:

```
#1 ATG ACG AGG TCC TTG TTT TTC (SEQ ID NO: 1)           pos 213-233

#2 GCT CCT GAT ACG ACA GCG (SEQ ID NO: 2)               pos 2403-2386

#3 GCC ATG GAT CAG GCC GGC AAG AGC CCG (SEQ ID NO: 3)   pos 663-683

#4 TGG ATC CTC AGA ACG AGC CGC TGG T (SEQ ID NO: 4)     pos 2258-2238
```

The positions refer to the sequence for mta found in GenBank accession number X16732. The primers with the higher number first are antisense primers and the sequences are the complementary sequences. In bold are represented nucleotides which are not complementary to the template DNA, and underlined are introduced restriction sites.) Primer #3 introduces a unique Nco1 site, and primer #4 a BamHI site which are used for the following cloning in the expression vector pBAD/gIII (Invitrogen).

A first PCR amplification using the following combination of primers was performed:

reaction 1 #1+#2 giving a fragment on 2190 bp with 50–150 ng genomic IAM1520 DNA as template, using the Expand DNA poly-merase (Boehringer Mannheim; Germany) according to the instructions of the manufacturer and the following amplification protocol:

94° C. 2 min, (94° C. 1 min, 58° C. 2 min, 72° C. 2 min) for 35 cycles and finally 72° C. 5 min.

A 2190 bp fragment was isolated from gel using the 'gene clean kit' (BIO101; California). The fragment was used as template DNA in a second PCR with the following primer combination:

reaction 2 #3+#4 giving a fragment on 1605 bp using the same amplification protocol as described above.

A 1605 bp fragment was purified and cloned into pCR-BLUNT vector (Invitrogen) according to the instructions of the manufacturer. The sequence of the cloned fragment was confirmed by sequencing using the single dye sequencing technology and a ALF sequencer (Pharmacia; Sweden) using the universal and reverse primers, and four labeled internal primers.

```
CAT CGT AGA GCA CCT CCA (SEQ ID NO: 5)       999-982

GAT CAT CAA GGA CTG GTC C (SEQ ID NO: 6)     1382-1400

CTT GAG AGC GAA GTC GAA C (SEQ ID NO: 7)     1439-1421

GAC TTC ATC CGC CAG CTG AT (SEQ ID NO: 8)    1689-1708
```

The positions refer to the sequence for mta found in GenBank accession number X16732. The primers with the higher number first are antisense primers and the sequences are the complementary sequences.

After confirming the sequence, the mta gene was cloned into the expression vector pBAD/gIII (Invitrogen). The mta gene was released from pCR-BLUNT by digestion with BamHI followed by blunting with Klenow fragment and digestion with Ncol, and a 1602 bp fragment was purified. The expression vector pBAD/gIII was digested with Ncol and Pmel and purified. After ligation the obtained expression construct was transformed into *Escherichia coli* MC1061 cells, and the protein was expressed according to the pBAD/gIII manual (Invitrogen).

Example 4
Comparison of the Effect of a Non-maltogenic and a Maltogenic Exoamylase on Starch Retrogradation Sweet potato β-amylase (EC 3.2.1.2; obtainable from Sigma with product no. A7005) is a maltogenic exoamylase releasing maltose from the non-reducing ends of starch. The thermostability of this maltogenic exoamylase is similar to that of *P. saccharophila* non-maltogenic exoamylase as indicated by the residual activities after incubation for 15 minutes at temperatures from 45 to 75° C. in 50 mM sodium citrate, 5 mM calcium chloride, pH 6.5 (Table 4).

TABLE 4

Residual activities of sweet potato β-amylase and
*P. saccharophila* non-maltogenic exoamylase atter incubation
at increasing temperatures (in %)[a]

| Incubation temperature (° C.) | 45 | 50 | 55 | 60 | 65 | 70 | 75 |
|---|---|---|---|---|---|---|---|
| Sweet potato β-amylase activity (%) | 100 | 117 | 55 | 12 | 5 | 4 | 4 |
| *P. saccharophila* exoamylase activity (%) | 100 | 68 | 29 | 10 | 7 | 6 | 6 |

Activity after incubation at 45° C. set to 100%.

The effects of both enzymes on starch retrogradation have been tested by DSC analysis of the baked and stored products from model system doughs as described in "Assays for measurement of retrogradation and staling". For this test 485 units of *P. saccharophila* non-maltogenic exoamylase and 735 units of sweet potato β-amylase assayed according to "Amylase assay protocol" were used in the doughs. The doughs were prepared of 50 g of standard Danish wheat flour (Danisco 98022) with 30.7 ml 50 mM sodium citrate, 5 mM calcium chloride, pH 6.5 without (control) or with enzymes added.

After 7 days of storage the amount of retrograded amylopectin was quantified by measuring its melting enthalpy. By statistical analysis it was found that both enzymes significantly reduce starch retrogradation (Table 5); i.e. *P. saccharophila* non-maltogenic exoamylase reduces the amount of retrograded amylopectin on day 7 to 86% (1.77 J/g) whereas sweet potato β-amylase lowers it to 96% (1.96 J/g) of the control (2.05 J/g). In conclusion, *P. saccharophila* non-maltogenic exoamylase is clearly much more efficient for reducing retrogradation and staling than the maltogenic amylase with a comparable thermostability.

TABLE 5

Effect of *P. saccharophila* non-maltogenic exoamylase
(PS4) and sweet potato β-amylase (SP2) on starch retro-
gradation based on measuring the melting enthalpy of retrograded
amylopectin (in J/g) 7 days after baking Multiple Range Tests for Enthalpy by Treatment Method: 95,0 percent LSD

| Treatment | Count | Mean |
|---|---|---|
| PS4 | 13 | 1,77154 |
| SP2 | 22 | 1,92273 |
| Control | 6 | 2,05167 |

| Contrast | Difference | +/- Limits |
|---|---|---|
| Control - PS4 | *0,280128 | 0,0941314 |
| Control - SP2 | *0,0889394 | 0,087641 |
| PS4 - SP2 | *-0,191189 | 0,06672 |

*denotes a statistically significant difference.

This table applies a multiple comparison procedure to determine which means are significantly different from which others. The bottom half of the output shows the estimated difference between each pair of means. An asterisk has been placed next to 3 pairs, indicating that these pairs show statistically significant differences at the 95,0% confidence level. The method currently being used to discriminate among the means is Fisher's least significant difference (LSD) procedure.

EXAMPLE—SECTION B

Materials and Methods
Materials

Amylopectin and amylose from corn, corn starch, carboxymethylcellulose (CMC), bovine serum albumine (BSA), dextran, pullulan, maltose, maltotriose, and a mixture of maltotetraose to maltodecaose were obtained from Sigma Chemical Co., St. Louis, U.S.A. Soluble starch was obtained from Merck KGaA, Darmstadt, Germany. Yeast extract and tryptone were obtained from Difco Laboratories, Detroit, USA. Whole brown rice from Neue Allgemeine Reisgesellschaft mbH, Hamburg, Germany was used. Pharmaceutical grade α-, β-, and γ-cyclodextrin were obtained from Wacker Chemie Danmark Aps, Glostrup, Denmark. Maltotetraose was prepared as described previously [32]. All chemicals were, unless stated otherwise, of analytical grade.

Isolation of *B. clausii* BT-21

The strain was isolated from a soil sample collected in Assens, Denmark, identified by DSMZ (Deutsche Sammlung von Mikroorganismen und Zellkulturen GmbH, Braunschweig, Germany)

Production of the enzyme

*B. clausii* BT-21 was grown in an optimised liquid medium composed of 2.0% soluble starch from potato, amylopectin from corn, corn starch, or whole brown rice, 0.5% yeast extract, 0.5% tryptone, 0.1% $KH_2PO_4$, 0.1%, $Na_2HPO_4$, 0.02% $MgSO_4.7H_2O$ , 0.02% $CaCl_2.2H_2O$, and 0.1% $(NH_4)_2 SO_4$. After autoclaving, a sterile $Na_2CO_3$ solution was added to a final concentration of 1% (approximately pH 10). A 1 mL spore suspension in glycerol (stored at −80° C.) was used to inoculate 100 ml of the actual medium and incubated at 45° C. for 18 h in a shaking incubator (New Brunswick Scientific, Edison, N.J., U.S.A.) at 200 rpm. Two mL of this culture was used to inoculate a shake flask with 200 mL medium and incubated at 45° C. in a shaking incubator. Aliquots were taken in regular intervals and the OD at 600 nm was measured to determine the growth of the strain in the media. Samples (4 mL) were centrifuged at 9600 rpm for 10 min at 4° C. and the pH and amylase activity was determined. All growth experiments were carried out in triplicate. The mean value ($X=(\Sigma^n_{i=1}X_i)/n$) and the standard deviation values (std.=$\sqrt{(\Sigma^n_{i=1}(X_i-X)/(n-1))}$) were determined.

Purification of the Product-specific Amylase

After growth of *B. clausii* BT-21 on whole brown rice for 52 h, the cells and the whole rice grains were removed from the extracellular fluid (1000 mL) by centrifugation at 9600 rpm for 15 min at 4° C. The product-specific amylase was purified using an affinity gel prepared by covalently binding β-cyclodextrin to an epoxy-activated sepharose 6B matrix (Pharmacia Biotech, Uppsala, Sweden) [33]. The extracellular cell-free supernatant was incubated with 12 g of gel while shaking supernatant was then removed by centrifugation at 9600 rpm for 10 min at 4° C. Unbound protein was removed by washing the gel with 75 mL 50 mM phosphate buffer pH 8.0 followed by centrifugation. The washing step was repeated 7 times. Bound protein was eluted with 45 mL of 50 mM phosphate buffer pH 8.0 containing 10 mM α-cyclodextrin followed by centrifugation. The elution step was repeated 4 times. α-Cyclodextrin was used for elution of the enzyme, since β- and γ-cyclodextrin interfered with the protein determination method of Bradford (1976) [34]. The α-cyclodextrin was then removed by dialysis (6–8 kDa Spectra/Por dialysis membrane, The Spectrum Companies, Gardena, Calif., U.S.A.) against 5 L 10 mM triethanolamin pH 7.5 while stirring at 4° C. The buffer was changed after 2 h followed by an additional 12 h of dialysis. The dialysis bags were placed in CMC to concentrate the sample. Ten mL were applied to a HiTrap Q column (5 mL prepacked, Pharmacia Biotech, Uppsala, Sweden) using a FPLC-system (Pharmacia, Uppsala, Sweden). The proteins were eluted at the rate of 1.0 mL/min with 25 mL 10 mM triethanolamin pH 7.5 followed by a gradient of 20 mM NaCl/min in 10 mM triethanolamin pH 7.5. The enzyme was eluted at 0.5 M NaCl. The protein content was estimated by the method of Bradford, (1976) [34] using the BIO-RAD Protein Assay (Bio-Rad Laboratories, Hercules, Calif., USA). BSA was used as standard.

Gel electrophoresis

15 μL samples were analysed by native tris-glycine gel, 10%, as described by [35]. The gel was then placed in 50 mM phosphate buffer at pH 6.5 and shaken for 30 min. A 1% (w/v) soluble starch solution was incubated with the gel while shaking for 45 minutes. After washing in buffer solution, the gel was incubated with an iodine solution (4 mM $I_2$, 160 mM KI) and decoloured with buffer. Destained bands indicated starch hydrolysis activity.

SDS-PAGE (10%) was performed according to [36] followed by silver staining [37]. A SDS-PAGE broad range molecular weight standard (Bio-Rad laboratories, Hercules, Calif., U.S.A.) was used.

Enzyme Assay

Two ml soluble starch solution (1.25%) in 0.1 M borate buffer pH 10.0 was incubated with 0.5 mL enzyme solution for 2 h at 45° C. The reaction was stopped by boiling the mixture for 10 min. The formation of reducing sugars was determined with the $CuSO_4$/bicinchonate assay [38] and calculated as mM maltose equivalent formed. One unit of activity corresponded to the amount of enzyme that produced 1 μmol maltose equivalent/min at pH 10.0 and 45° C.

Enzyme Characterisation

For the determination of the temperature optimum, the purified enzyme was incubated in a final concentration of 1% soluble starch in 0.1 M borate buffer pH 10.0 (with or without the addition of 5 mM $CaCl_2$) for 15 min at temperatures from 30° C. to 90° C. Determination of the temperature stability was performed by incubation of the purified enzyme in 50 mM glycine-NaOH buffer pH 9.5 containing 5 mM $CaCl_2$ for 30 min at 30, 40, 50, 55, 60, 70, 80, and 90° C. Residual activity was determined by incubation of the heat-treated enzyme in a final concentration of 1% soluble starch in 50 mM glycine-NaOH buffer pH 9.5 at 55° C. for 15 min. The pH optimum was determined by incubation of the purified enzyme in a final concentration of 1% soluble starch in different buffers at 55° C. for 15 min. The buffers used were 50 mM citrate (pH 4.0 to 6.0), 50 mM tris-maleate (pH 6.5 to 8.5), and 50 mM glycine-NaOH (pH 9.0 to 11.0).

An $I_2$-KI solution (0.02% $I_2$ and 0.2% KI) was prepared according to Fuwa, 1954 [39]. The starch-iodine blue colour formation was measured in duplicates with the following modifications. A sample of 500 μL was withdrawn from the enzymatic hydrolysis of soluble starch at different time intervals. Then 250 μL HCl and 250 μL $I_2$-KI-solution were added and mixed. Deionised water (4.0 mL) was added and mixing was repeated. The formation of a blue colour was measured spectrophotometrically at 600 nm.

The hydrolysis of different substrates by the purified enzyme was tested with soluble starch from potato, amylopectin from corn, dextran, pullulan (1%), amylose (0.1%), and 10 mM α-, β-, and γ-cyclodextrin. The substrates were dissolved in 50 mM glycine-NaOH buffer with 5 mM $CaCl_2$ at pH 9.5 and the purified enzyme was added (505 mU/mL). The various substrates were incubated at 55° C. and samples were withdrawn at different time intervals. The reaction was stopped by boiling for 10 min and the samples were analysed as described below.

The hydrolysis of malto-oligosaccharides by the purified enzyme was tested with maltose, maltotriose, and maltotetraose in a final concentration of 2 mM and a mixture of maltotetraose to maltodecaose (5 mM). The malto-oligosaccharides were dissolved in 50 mM borate buffer with 5 mM $CaCl_2$ at pH 9.5 and the purified enzyme was added (147 mU/mL). The substrates were incubated at 55° C. and samples were withdrawn at different time intervals. The reaction was stopped by boiling for 10 min and the samples were analysed as described below.

Analysis of Hydrolysis Products

Hydrolysis products were detected using high performance anion exchange chromatography with pulsed amperometric detection (HPAEC-PAD). A CarboPac PA-1 column (Dionex Corporation, Sunnyvale, Calif., U.S.A) was used with a gradient of 1.0 M Na-acetate from 0 to 60% over 30 min in 100 mM NaOH and a flow rate of 1.0 mL/min on a Dionex DX-300 or DX-500 system. Starch hydrolysis products were identified by comparison of their retention times with glucose, maltose, maltotriose, maltotetraose, maltopentaose, and maltohexaose. Since the retention times of homologous linear malto-oligosaccharides increases with the degree of polymerisation, linear malto-oligosaccharides of intermediate DP could be easily identified [40, 41].

Results and Discussion

Identification of B. clausii BT-21.

According to its fatty acid composition, the strain showed similarity to the genus Bacillus. A partial sequencing of the 16SrDNA showed a similarity of 99.4% to B. clausii. The physiological properties of the alkali-tolerant strain confirmed this identification.

Production of Amylase Activity by B. clausii BT-21.

Soluble starch from potato, corn starch, amylopectin from corn and whole brown rice resulted in different levels of extracellular amylase activity in the medium. While, corn starch contain more lipids and no phosphorus compared to potato starch amylopectin from corn has a highly branched structure containing α-D-(1→6) O-glycosidic linkages. These three types of starch are accessible for enzymes after heat gelatinisation, while whole brown rice contains a less accessible starch encapsulated in the rice grains. The amylase activities in the extracellular fluid of liquid cultures with the different starch substrates are shown in FIG. 1. The highest amylolytic activity was obtained with whole brown rice as a substrate. This indicates that the presence of a less accessible starch substrate resulted in an increased production of extracellular amylolytic activities by B. clausii BT-21. Similar results were obtained with wheat bran, which was however difficult to remove from the extracellular fluid prior to purification of the enzyme. Carbon sources such as galactose, glycogen, and inulin have previously been reported as suitable for amylase production by B. licheniformis[27] and soluble starch has been found as the best substrate for the production of an amylase by B. stearothermophilus [28]. However, none of these studies has included a less accessible starch substrate.

Purification of the Product-specific Amylase

The enzyme was purified by affinity chromatography with β-CD Sepharose 6B followed by anion-exchange chromatography (Table 6).

TABLE 6

Purification of the product-specific amylase from *B. clausii* BT-21.

| | Volume (mL) | Activity (mU/mL) | Total activity (mU) | Total protein (mg) | Specific activity (mU/mg protein) | % recovery | Purification factor |
|---|---|---|---|---|---|---|---|
| Extracellular fluid | 4000 | 155 | 620,000 | 424 | 731 | 100 | 1 |
| β-CD affinity chromatography | 704.5 | 88 | 62,137 | 8.5 | 3,647 | 10.0 | 5 |
| Concentration and dialysis | 172.6 | 254 | 43,840 | 4.8 | 4,581 | 7.1 | 6.3 |
| Anion-exchange chromatography | 215 | 251 | 54,051 | 2.0 | 13,493 | 8.7 | 18.5 |

Activity stained native PAGE indicated the presence of 3 amylolytic activities in the extracellular fluid. The product-specific enzyme was completely separated from the other amylolytic activities after β-CD affinity chromatography followed by anion-exchange chromatography. SDS-PAGE of the purified enzyme preparation indicated that the product-specific amylase has been purified to homogeneity and has an apparent molecular weight of approximately 101 kDa. Cyclodextrin sepharose 6B affinity chromatography has been previously used for the purification of an α-amylase as a final purification step after removal of other amylases by anion-exchange chromatography [29]. The enzyme recovery of 8.7% and the purification factor of 18.5 obtained for the product-specific amylase were similar to the values reported by these authors.

Characterisation of the Product-specific Amylase

The purified enzyme showed an optimum of activity at pH 9.5 (FIG. 2) while optimum temperature for its activity was at 55° C. with or without the presence of 5 mM $CaCl_2$ (FIG. 3). The thermostability of the enzyme at pH 9.5 in the presence of 5 mM $CaCl_2$ is shown in FIG. 4. At temperatures above 55° C., the enzyme lost 75% of its maximum activity during a 30 min incubation period. Five other product-specific amylases forming maltohexaose [23], maltopentaose [24], and maltotetraose [26] also show an alkaline pH optimum. The molecular weight of these enzymes were estimated to be 59, 73 and 80 kDa [23], 180 kDa [24], and 97 kDa [26] while the product-specific amylase from *B. clausii* BT-21 showed an estimated molecular weight of 101 kDa. Most of the product-specific amylases and α-amylases show a lower molecular weight in the range of 50–65 kDa [3, 16, 17, 19, and 21]. The temperature optimum of about 55° C. was similar to the ones reported for the above product-specific amylases [23, 24, and 26].

The purified product-specific amylase hydrolysed soluble starch after 1 h of incubation mainly to maltohexaose and maltopentaose (52% and 19% of total hydrolysed products) as the main initial products of low DP (FIG. 5). After 2 h of incubation, the amount of maltohexaose and after 4 h the amount of maltopentaose decreased while the amounts of maltotetraose, maltotriose, maltose and glucose increased. These products accumulated after prolonged hydrolysis indicating that they were not further hydrolysed. After 24 h of starch hydrolysis, the amounts of malto-oligosaccharides was (3%) maltohexaose, (4%) maltopentaose, (41%) maltotetraose, (13%) maltotriose, (16%) maltose and (4%) glucose. The high performance anion-exchange chromatography with pulsed amperometric detection (HPAEC-PAD) trace obtained after 30 min starch hydrolysis (FIG. 6) shows that starch hydrolysis products larger than maltohexaose (DP6) were absent. A time course study of the hydrolysis of soluble starch by a maltohexaose-forming product-specific amylase has also shown that maltohexaose was produced preferentially in the early stage of hydrolysis [23]. Kim et al (1995) [26] found that the initial hydrolysis product after 1 h hydrolysis of starch with a maltotetraose-forming product-specific amylase was mainly maltohexaose (54%) followed by a gradual increase in the amounts of maltotetraose and maltose while the amount of maltohexaose decreased. After 20 h, the composition of malto-oligosaccharides had changed to 0.6% maltohexaose, 1.3% maltopentaose, 53.2% maltotetraose, 8.3% maltotriose, 27.6% maltose and 9% glucose.

To examine further the mode of action of the enzyme during starch hydrolysis, different substrates were incubated with the purified enzyme (Table 7).

TABLE 7

Malto-oligosaccharides in the range DP1 to DP6 formed by the hydrolysis of various starch substrates by the purified product-specific enzyme (67 mU/mL). Data are indicated as wt % glucose formed compared to the initial amount of substrate

| Substrate | Hydrolysis time (min) | Product formed (%) | | | | | |
|---|---|---|---|---|---|---|---|
| | | DP1 | DP2 | DP3 | DP4 | DP5 | DP6 |
| Soluble starch (1%) | 15 | 0 | 0 | 0 | <0.1 | 0.9 | 7.2 |
| | 240 | 0 | 0 | 0 | 0.6 | 7.0 | 17.8 |
| Amylose (0.1%) | 15 | 0.2 | 0 | 0 | 0 | 2.4 | 13.6 |
| | 240 | 1.5 | 0 | 4.1 | 7.7 | 6.3 | 20.0 |
| Amylopectin (1%) | 15 | <0.1 | 0 | 0 | 0 | 0.8 | 3.6 |
| | 240 | <0.1 | 0.5 | 0.1 | 0.9 | 9.2 | 24.8 |

Starches are composed of amylose (20–30%) and amylopectin (80–70%). Amylose is an α-D-(1→4) O-glycosidically linked linear glucan, while amylopectin is a branched glucan due to the presence of α-D-(1→6) O-glycosidic linkages in the molecule. The product-specific amylase most readily hydrolysed amylopectin indicated by the formation of maltopentaose (9.2%) and maltohexaose (24.8%) compared to soluble starch (7% and 17.8%) and amylose (6.3% and 20%).The enzyme did not hydrolyse pullulan, an α-(1→6) O-glycosidic linked glucan composed of a maltotriose backbone, or dextran, an α-(1→6) O-glycosidically linked glucan with branches attached to 0–3 of the backbone chain units. α-, β-, And γ-cyclodextrins, cyclic malto-oligosaccharides composed of 6, 7, and 8 glucose units were also not hydrolysed even after 24 h incubation.

The results obtained on dextran indicated that no α-(1→6) O-glycosidic linkages could be cleaved by the product-specific amylase. The lack of activity on pullulan indicated that the product-specific amylase could not bypass α-(1→6) O-glycosidic linkages next to three glucose units or attack any of these three glucose units. The lack of hydrolysis on α-, β-, or γ-cyclodextrins indicated that the product-specific amylase hydrolysed starch by an exo-type of cleavage mechanism [30]. The HPAEC-PAD trace (FIG. 6) also indicated a cleavage mechanism of the exo-type, since starch hydrolysis products larger than DP6 were absent.

To examine further the enzyme cleavage action on soluble starch, the starch-iodine blue colour formation was plotted against the production of reducing sugars (FIG. 7). The slope of the curve is indicating the prevalent type of cleavage mechanism of amylolytic starch hydrolysis [31]. An endo-acting enzyme will produce a slope with a smaller value compared to an exo-acting enzyme. A small value of the slope is the result of a fast reduction of the starch-iodine blue colour complex due to random amylolytic activity, indicated by the α-amylase from A. oryzae (the slope is −61). The extracellular enzyme preparation from P. stutzeri showed evidence for a prevalent exo-acting cleavage mechanism indicated by a larger slope value (the slope is −13). The purified product-specific amylase showed a slope value of −6, indicating exo-activity.

The mode of action of hydrolysis of substrates with low DP by the product-specific amylase was examined by incubation with such substrates. Maltose, maltotriose, and maltotetraose were not hydrolysed by the purified B. clausii BT-21 amylase. This confirms the results obtained on soluble starch, that these products are accumulating and therefore considered as end products of the hydrolysis.

The product-specific amylase activity on a mixture of malto-oligosaccharides from DP4 to DP10 was studied by a time course experiment. The change of the peak areas obtained by the HPAEC-PAD corresponded to the formation or a hydrolysis of malto-oligosaccharides. The formation of maltohexaose (DP6) and the simultaneous decrease in the amount of DP7, DP8, DP9, and DP10 confirmed the maltohexaose forming ability of the enzyme. However, steady state conditions were reached and the further degradation of DP6 as found by starch hydrolysis was not detected even after 7 days of hydrolysis. The concentration of DP6 was much lower than the one obtained at the starch hydrolysis and indicated that a certain amount of maltohexaose was required for the formation of maltotetraose and maltose to proceed.

The starch hydrolysis by the B. clausii BT-21 product specific amylase was found to resemble a two step procedure. This procedure included an initial hydrolysis of starch to mainly maltohexaose and small amounts of maltopentaose, which were further hydrolysed to mainly maltotetraose and maltose accumulating after extensive hydrolysis. The second hydrolysis step to maltotetraose and maltose seemed to be limited by the preliminary hydrolysis of the larger substrate to maltohexaose, since a concentration dependence seemed to a regulator for the second step to proceed.

Baking Experiment

A baking experiment was performed with the product-specific amylase. Doughs were prepared with 10 g of standard Danish wheat flour (Danisco 98078) and 6.2 ml 0.2 M NaOH-glycine buffer, pH 10 without (control) or with 40 units of the enzyme (assayed at 45° C. and pH 10 as described in Materials and Methods of Section B), baked and analysed by DSC after storage according to "Assays for measurement of retrogradation and staling". As shown in Table 8 the enzyme significantly reduces the amount of retrograded amylopectin found day 7 after baking which indicates that it has a significant antistaling effect.

TABLE 8

Effect of B. clausii product-specific amylase on starch retrogradation based on measuring the melting enthalpy of retrograded amylopectin (in J/g) 7 days after baking Multiple Range Tests for Enthalpy by Treatment Method: 95,0 percent LSD

| Treatment | Count | Mean |
| --- | --- | --- |
| Enzyme | 16 | 2,44375 |
| Control | 16 | 2,56 |

| Contrast | Difference | +/− Limits |
| --- | --- | --- |
| Control - Enzyme | *0,11625 | 0,0491094 |

*denotes a statistically significant difference.

Crumb samples of the baked products frozen after the baking have been extracted with distilled water (1 g baked product/10 g water, stirred for 1 h and centrifuged) and analysed by HPAEC-PAD as described above to detect the starch hydrolysis products formed by the enzyme during the baking of the doughs. Relative to the control accumulation of maltotetraose, maltopentaose, maltohexaose and maltoheptaose was found as result of the activity of this enzyme.

Summary Section

The present invention discloses a process for making bakery products, as well as amylases suitable for use in such a process.

Preferred embodiments of the present invention are now presented by way of numbered paragraphs.

REFERENCES

[1]. K. H. Park, Food Sci. Ind. 25 (1992) 73–82.

[2]. M. Okada and T. Nakakuki, Oligosacchardes: production, properties and application, in F. W. Schenck and R. E. Hebeda (Eds.), Starch hydrolysis products worldwide technology, production and application, VCH Publishers, New York, 1992, pp 335–366.

[3]. W. M. Fogarty, Microbial amylases, in W. M. Fogarty (Ed.), Microbial enzymes and biotechnology, Applied Science, London, 1983, pp. 1–92.

[4]. W. M. Fogarty and C. T. Kelly, Starch-degrading enzymes of microbial orgin, in M. J. Bull (Ed. ), Progress in industrial microbiology, Vol. 15, Elsevier Scientific 1979, pp. 87–150.

[5]. K. Kainuma, S. Kobayashi, T. Ito, and S. Suzuki, FEBS Letters, 26 (1972) 281–285.

[6]. N. Monma, T. Nakakuki, and K. Kainuma, Agric. Biol. Chem. , 47 (1983) 1769–1774.

[7]. J. F. Kennedy and C. A. White, Starch/Stärke 31 (1979) 93–99.

[8]. Y. Takasaki, Agric. Biol. Chem. 46 (1982) 1539–1547.

[9]. H. Taniguchi, C. M. Jae, N. Yoshigi, and Y. Maruyama, Agric. Biol. Chem. 47 (1983) 511–519.

[10]. H. Taniguchi, Maltohexaose-producing amylase of Bacillus circulans F-2 in R. B. Friedman (Ed. ) Biotechnology of amylodextrin oligosaccharides. ACS Symp.Ser. 458. American Chemical Society, Washington DC, 1991, pp 111–124.

[11]. F. Bealin-Kelly, C. T. Kelly, and W. M. Fogarty, Biochem. Soc. Trans. , 18 (1990) 310–311.

[12]. W. M. Fogarty, F. Bealin-Kelly, C. T. Kelly, and E. M. Doyle, Appl. Microbiol. Biotechnol. , 36 (1991) 184–489.

[13]. N. Saito, Archives. Biochem. Biophys., 155 (1973) 290–298.
[14]. H. Okemoto, S. Kobayashi, M. Monma, H. Hashimoto, K. Hara, and K. Kainuma, Appl. Microbiol. Biotechnol., 25 (1986) 137–142.
[15]. O. Shida, T. Takano, H. Takagi, K. Kadowaki, and S. Kobayashi, Biosci., Biotechnol., Biochem. 56 (1992) 76–80.
[16]. (There is no ref. [16])
[17]. Y. Sakano, Y. Kashiwagi, and T. Kobayashi, Agric. Biol. Chem., 46 (1982) 639–646.
[18]. Y. Takasaki, H. Shinohara, M. Tsuruhisa, S. Hayashi, K. Imada, Agric. Biol. Chem. 55 (1991) 1715–1720.
[19]. W. M. Fogarty, C. T. Kelly, A. C. Bourke, and E. M. Doyle, Biotechnol. Lett. 16 (1994) 473–478.
[20]. K. Wako, S. Hashimoto, S. Kubomura, A. Yokota, K. Aikawa, and J.
Kamaeda, J. Jap. Soc. Starch. Sci 26 (1979) 175–181.
[20]. Y. Takasaki, Agric. Biol. Chem. 49 (1985) 1091–1097.
[22]. (There is no ref. [22])
[23]. T. Hayashi, T. Akiba, and K. Horikoshi, Appl. Microbiol. Biotechnol. 28 (1988b) 281–285.
[24]. G. Schmid, A. Candussio, and A. Bock, U.S. Pat. No. 5,304,723 (1994).
[25]. M. A. Mc Tigue, C. T. Kelly, E. M. Doyle, and W. M. Fogarty, Enzyme Microb. Technol., 17 (1995) 570–573.
[26]. T. U. Kim, B. G. Gu, J. Y. Jeong, S. M. Byun, and Y. C. Shin, Appl. Environm. Microbiol. 61 (1995) 3105–3112.
[27]. A. K. Chandra, S. Medda, and A. K. Bhadra, J. Ferment. Technol., 58, (1980), 1–10.
[28]. R. A. K. Srivastava and J. N. Baruah, Appl. Environ. Microbiol. 52 (1986) 179–184.
[29]. V. Planchot and P. Colonna, Carbohydr. Res., 272 (1995) 97–109.
[30]. J. F. Robyt and W. J. Whelan, The α-amylases in J. A. Radley (Ed.) *Starch and its derivatives*, 4. ed. Chapman and Hall, London, 1968, pp.430–476.
[31]. M. Ohnishi and K. Hiromi, *General considerations for conditions and methods of amylase assay* in The Amylase Research Society of Japan (Ed.) *Handbook of amylases and related enzymes. Their sources, isolation methods, properties and applications*. Pergamon, Oxford, 1988, pp.10–14.
[32]. L. Duedahl-Olesen, W. Zimmermann, and J. A. Delcour, Cereal Chemistry (1999) In press.
[33]. K. L. Larsen, L. Duedahl-Olesen, H. J. S. Christensen, F. Mathiesen, L. H. Pedersen, and W. Zimmermann, Carbohydr. Res. 310 (1998) 211–219.
[34]. M. M. Bradford, Anal. Chem., 72 (1976) 248–254.
[35]. Novex, Precast Gel Instructions. NOVEX, San Diego, Calif., USA
[36]. Mini Protean II Electrophoresis Cell instructions manual. Bio-Rad laboratories, Hercules, Calif., U. S. A.
[37]. H. Blum, H. Beier, and H. J. Gross, Electrophoresis (1987) 93–99.
[38]. L. H. Pedersen, H. J. S. Christensen, F. Mathiesen, K. L. Larsen, and W. Zimmermann, Starch, 49 (1997) 250–253.
[39]. H. J. Fuwa, J. Biochem., 41 (1954) 583–603.
[40]. Y. C. Lee, J. Chormatogr. A, 720 (1996) 137–149.
[41]. R. N. Ammerall, G. A. Delgado, F. L. Tenbarge, and R. B. Friedmann, Carbohydr. Res. 215 (1991) 179–192.

What is claimed is:

1. A process for making a bakery product comprising:
   (a) adding to a starch medium a non-maltogenic exoamylase that hydrolyses starch by cleaving off one or more linear malto-oligosaccharides, predominantly comprising from four to eight D-glucopyranosyl units, from non-reducing ends of amylopectin side chains; and
   (b) baking the starch medium before, during or after step (a).

2. A process according to claim 1, wherein the non-maltogenic exoamylase has an endoamylase activity of less than 0.5 endoamylase units (EAU) per unit of exoamylase activity.

3. A process according to claim 1, wherein the starch medium comprises wheat flour or rye flour or mixtures thereof.

4. A process according to claim 1, wherein the non-maltogenic exoamylase yields, in a waxy maize starch incubation test, one or more hydrolysis products comprising one or more linear malto-oligosaccharides of from one to ten D-glucopyranosyl units, and wherein at least 60% by weight of the linear malto-oligosaccharides of from one to ten D-glucopyranosyl units consist of from three to eight D-glucopyranosyl units.

5. A process according to claim 1, wherein at least 60% of the hydrolysis product is maltotetraose, maltopentaose, maltohexaose, maltoheptaose, or maltooctaose.

6. A process according to claim 5, wherein at least 60% of the hydrolysis product is maltotetraose.

7. A process according to claim 6, wherein the non-maltogenic exoamylase is obtained from *Pseudomonas saccharophila*.

8. A process according to claim 7, wherein the non-maltogenic exoamylase is encoded by a DNA sequence comprising GenBank accession number X16732.

9. A process according to claim 5, wherein at least 60% of the hydrolysis product consists of maltohexaose.

10. A process according to claim 9, wherein the non-maltogenic exoamylase is obtained from *Bacillus clausii*.

11. A process according to claim 10, wherein the non-maltogenic exoamylase has a molecular weight of about 101,000 Da as estimated by sodium dodecyl sulphate polyacrylamide electrophoresis.

12. A process according to claim 11, wherein the non-maltogenic exoamylase has an optimum of activity at pH 9.5 and 55° C.

13. A process for making a bakery product comprising:
    (a) providing a non-maltogenic exoamylase that hydrolyses starch by cleaving off one or more linear malto-oligosaccharides predominantly comprising from four to eight D-glucopyranosyl units from non-reducing ends of amylopectin side chains;
    (b) mixing the non-maltogenic exoamylase with flour, water and leavening agent under dough forming conditions; and
    (c) baking the dough.

14. A bakery product obtained by the process according to claim 1.

15. A bakery product obtained by the process according to claim 13.

* * * * *